(12) United States Patent
Yamamoto et al.

(10) Patent No.: US 7,037,685 B2
(45) Date of Patent: *May 2, 2006

(54) DNA ENCODING LOYPEPTIDES HAVING INTERFERON-γ INDUCING ACTIVITY

(75) Inventors: Kozo Yamamoto, Okayama (JP); Iwao Okamoto, Okayama (JP); Masashi Kurimoto, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 213 days.

This patent is subject to a terminal disclaimer.

(21) Appl. No.: 10/260,576

(22) Filed: Oct. 1, 2002

(65) Prior Publication Data

US 2003/0092130 A1 May 15, 2003

Related U.S. Application Data

(62) Division of application No. 08/982,285, filed on Dec. 1, 1997, now Pat. No. 6,476,197.

(30) Foreign Application Priority Data

| Nov. 29, 1996 | (JP) | ................................... 8-333037 |
| Jan. 21, 1997 | (JP) | ................................... 9-20906 |
| Nov. 14, 1997 | (JP) | ................................... 9-329715 |
| Nov. 14, 1997 | (JP) | ................................... 10053503 |

(51) Int. Cl.
   *C12P 21/02* (2006.01)

(52) U.S. Cl. ............... 435/69.5; 435/320.1; 435/252.3; 435/325; 435/6; 536/23.5; 530/351

(58) Field of Classification Search ............... 435/69.5, 435/320.1, 252.3, 325, 6; 530/351
See application file for complete search history.

(56) References Cited

U.S. PATENT DOCUMENTS

| 4,518,584 | A | 5/1985 | Mark et al. |
| 5,776,731 | A | 7/1998 | Parnet et al. |
| 5,912,324 | A | 6/1999 | Okamura et al. |
| 6,214,584 | B1 | 4/2001 | Ushio et al. |

FOREIGN PATENT DOCUMENTS

| EP | 0712931 | 5/1996 |
| WO | 0692536 | 1/1996 |
| WO | 827189 | 1/1996 |
| WO | 0712931 | 5/1996 |
| WO | 8193098 | 7/1996 |
| WO | 8217798 | 8/1996 |
| WO | 8231598 | 9/1996 |
| WO | 0767178 | 4/1997 |
| WO | WO 9744468 | 11/1997 |
| WO | 0819757 | 1/1998 |
| WO | 0821005 | 1/1998 |

OTHER PUBLICATIONS

Balwill, "Cytokines in cancer therapy", *Oxford Medical Publications* (1989).
Laemili, Cleavage of structural proteins during the assembly of the head of bacteriophage T4, *Nature*, 227:680-685 (1970).
Horton et al., "G4ene splicing by overlap extension", *Methods in Enzymology*, 217:270-279 (1993).
Henco et al., "Structural relationship of human interferon alpha genes and pseudogenes", *J. Mol. Biol.*, 185:227-260 (1985).
Fujioka et al., "Combination of lymphokine-activated killer cells and interleukin-2 in treating metastatic renal cell carcinoma", *British Journal of Urology*, 73:23-31 (1994).
Hay et al., "ATCC cell lines and hybridomas", *American Type Culture Collection*, 8th edition (1994).
Shimada et al., "Basic techniques for the gene therapy", *Biomanual Up Series* (1996).
Yokota et al., "The experimental methods for the gene cloning", *Biomanual Series 3* (1993).
Kuroki et al., "The handbook for the cell engineering", *Saibo-Kogaku Handbook*, (1992).
"Riken Cell Bank", *Cell Line Catalog*, 9:77 and 234 (1996).
Okamura et al., *Nature*, 378:88-91 (1995).
Ushio et al., *J. Immunol.*, 156:4274-4279 (1995).

*Primary Examiner*—Lorraine Spector
*Assistant Examiner*—Dong Jiang
(74) *Attorney, Agent, or Firm*—Browdy and Neimark, PLLC

(57) ABSTRACT

Disclosed are created stable polypeptides which are capable of inducing the production of interferon-gamma by immunocompetent cells. The present polypeptides contain specific amino acid sequences usually derived from the wild-type polypeptides, being capable of the production of interferon-gamma, by replacing the cysteine(s) with different amino acid(s). The present polypeptides possess a stability and an activity of inducing the production of IFN-γ by immunocompetent cells, both of which are significantly higher than those of the wild-type polypeptides. In addition to the activity, the present polypeptides can exhibit remarkable activities of inducing the formation of killer cells and enhancing thier cytotoxicities. The present polypeptides are easily obtainable by the process according to the present invention using recombinant DNA techniques. Thus the present polypeptides are useful for agents to treat and/or prevent susceptive diseases such as viral diseases, infections, malignant tumors, and immunopathies.

11 Claims, 8 Drawing Sheets

Note: In the figure, the symbol "O—O" shows the time course upon the activity of a wild-type polypeptide; and the symbols "▼—▼", "▲—▲", "▽—▽", "◇—◇", "●—●", "■—■", and "△—△" show the time course upon the activity of the present polypeptides obtained by the methods in Examples A-1 to A-7, respectively.

Note: In the figure, the symbol "■—■" shows the time course upon the activity of a wild-type polypeptide; and the symbols "□—□" and "♦—♦" show the time course upon the activity of the present polypeptides obtained by the methods in Examples A-8 and A-9, respectively.

DNA ENCODING LOYPEPTIDES HAVING INTERFERON-γ INDUCING ACTIVITY

CROSS-REFERENCE TO RELATED APPLICATIONS

This is a division of application Ser. No. 8/982,285, filed Dec. 1, 1997, now issued as U.S. Pat. No. 6,476,197.

BACKGROUND OF THE INVENTION

1. Field of the Invention

The present invention relates to novel biologically active polypeptides, more particularly, artificially created polypeptides which are commonly capable of inducing the production of interferon-gamma (hereinafter abbreviated as "IFN-γ") by immunocompetent cells.

2. Description of the Prior Art

The present inventors successfully isolated some polypeptides which are capable of inducing the production of IFN-γ by immunocompetent cells, as well as cloned cDNAs which encode the polypeptides (hereinafter called "the wild-type polypeptides"); the relating inventions are disclosed in Japanese Patent Kokai Nos. 27,189/96 and 193,098/96 and Japanese Patent Application No. 67,434/96. It is known that the wild-type polypeptides usually contain SEQ ID NOs:1–3 as consensus partial amino acid sequences, and that they usually possess properties of inducing the formation of killer cells and enhancing their cytotoxicities, in addition to the property of inducing production of IFN-γ, a useful biologically active protein. Because of the properties, the use of the wild-type polypeptides as antiviral, antimicrobial, antitumor, and/or anti-immunopathic agents, etc. is in great expectation.

However, as described in Japanese Patent Application No. 67,434/96 by the present applicant, there is the problem that natural cells commonly do not enable producing the wild-type polypeptide in desired amounts. The present inventors energetically investigated the cause, revealing that the wild-type polypeptides usually exist in the form of precursor exhibiting no biological activity in natural cells. The precursor has been proved to be converted into an active form by the action of converting enzymes such as interleukin-1β converting enzymes, which is described in Japanese Patent Application Nos. 207,691/96 and 213,267/96 by the present applicant.

The wild-type polypeptides are probably instable, which would be involved in the above problem as another cause. Progress in recombinant DNA techniques of recent years have facilitated to remove and/or replace one or more amino acids in biologically active proteins to develop mutagenized polypeptides. However, even the progressed recombinant DNA techniques couldn't improve the stability of every protein with the inherent activity, unless taking trails and errors on the proteins individually.

SUMMARY OF THE INVENTION

In view of the foregoing, the first object of the present invention is to provide a polypeptide with significantly improved stability, while substantially retaining a biological activity of the wild-type polypeptide.

The second object of the present invention is to provide a process for producing the polypeptide.

The third object of the present invention is to provide a use of the polypeptide for a pharmaceuticals.

The present inventors energetically studied to attain the above objects, revealing that a polypeptide is more stable than the wild-type polypeptide, wherein the stale polypeptide contain an amino acid sequence derived either from a polypeptide containing the partial amino acid sequences of SEQ ID NOs:1–3 by replacing one or more of the cysteines with a different amino acid(s), or from the cysteine-replaced amino acid sequences by adding, removing and/or replacing one or more amino acids to and/or at position(s) excepting the position(s) where the cysteine(s) has been replaced; and that some of the stable polypeptides, in which the cysteine(s) have been replaced, exhibit an activity of inducing the production of IFN-γ by immunocompetent cells significantly higher than the wild-type polypeptides. These polypeptides proved to be easily produced in a desired amount by using recombinant DNA techniques and to exhibit less toxicities. Based on the above, the present polypeptides were confirmed to be effectively used not only as an IFN-γ inducer but also as a pharmaceutical.

The first object of the present invention is attainable by an isolated polypeptide which is capable of inducing the production of interferon-gamma by immunocompetent cells, said polypeptide containing either amino acid sequence wherein one or more cysteines are replaced with different amino acid(s) while leaving respective consensus sequences as shown in SEQ ID NOs:1–3 intact, or that wherein one or more amino acids are added, removed and/or replaced at one or more sites including those in the consensus sequences but excluding those of the replaced cysteine.

The second object of the present invention is attainable by a process for producing a polypeptide, which comprises the steps of culturing a cell containing a DNA encoding the present polypeptide to produce a polypeptide, and collecting the produced polypeptide from the resulting culture.

The third object of the present invention is attainable by an agent for susceptive diseases, which contains the present polypeptide as an effective ingredient.

BRIEF EXPLANATION OF THE ACCOMPANYING DRAWINGS

EXPLANATION OF SYMBOLS

Figure 1:
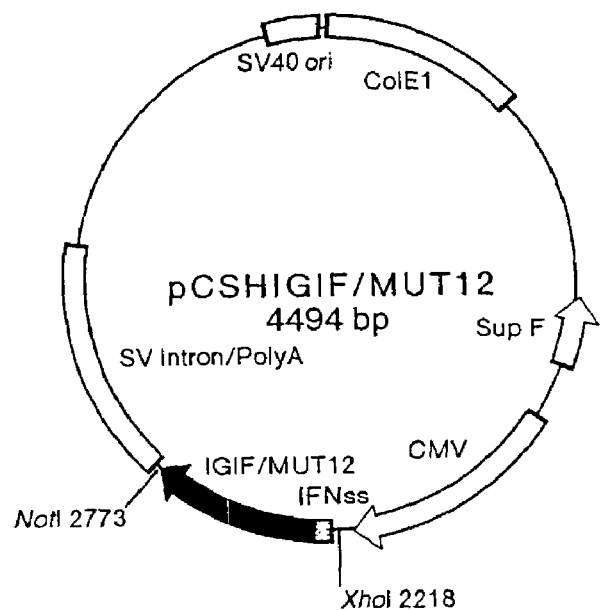
FIG. 1 is the restriction map of a recombinant DNA "pCSHIGIF/MUT12" encoding a polypeptide according to the present invention.

The symbol "CMV" indicates a cytomegalovirus promoter.

The symbol "IFNss" indicates a nucleotide sequence encoding the signal peptide of the subtype α2b of human interferon-α.

The symbols "IGIF/WT" and "mIGIF/WT" indicate cDNAs encoding any one of the wild-type polypeptides.

The symbols of "IGIF/MUT12", "IGIF/MUT21", "IGIF/MUT25", "IGIF/MUT32", "IGIF/MUT41", "IGIF/MUT35", "IGIF/MUT42", "mIGIF/MUT11" and "mIGIF/MUT12" indicate cDNAs each of which encodes one of the polypeptides according to the present invention.

DETAILED DESCRIPTION OF THE INVENTION

The followings are preferred embodiments according to the present invention. The polypeptides according to the present invention include all of the polypeptides which is capable of inducing production of interferon-gamma by immunocompetent cells, wherein said polypeptides contain either amino acid sequence wherein one or more cysteines are replaced with different amino acid(s) while leaving respective consensus sequences as shown in SEQ ID NOs: 1–3 intact, or that wherein one or more amino acids are added, removed and/or replaced at one or more sites including those in the consensus sequences but excluding those in the replaced cysteine. The different amino acids to replace the cysteine(s) are not restricted to any types, as far as the resulting polypeptide, containing an amino acid sequence replaced with the different amino acid(s), exhibits an activity of inducing production of IFN-γ by immunocompetent cells in the presence or absence of an appropriate cofactor, as the wild-type polypeptides containing SEQ ID NOs:1–3 as consensus partial amino acid sequences, and a stability significantly higher than that of the wild-type polypeptides. The different amino acids include serine, threonine, alanine, valine, leucine, isoleucine, histidine, tyrosine, phenylalanine, tryptophan, and methionine, among which the most preferable amino acid is serine or alanine. Embodiments of the amino acid sequences, containing SEQ ID NOs:1–3 as consensus partial amino acid sequences, in which one or more cysteines are to be replaced with different amino acid(s) are the wild-type polypeptides containing the SEQ ID NO:4 or 5. The SEQ ID NO:4 contains cysteines at the 38th, 68th, 76th, and 127th positions from the N-terminus. The SEQ ID NO:5 contains cysteines at the 7th, 75th, and 125th positions.

The present polypeptides include those containing the amino acid sequence of any one of SEQ ID NOs:6–12, which are derived from the wild-type polypeptide containing SEQ ID NO:4, those containing the amino acid sequence of SEQ ID NO:13 or 14, which are derived from the wild-type polypeptide containing the amino acid sequence of SEQ ID NO:5, and those containing an amino acid sequence derived from any one of SEQ ID NOs:6–14 by adding, removing, and/or replacing one or more amino acids to and/or at position(s) excepting the positions where the cysteine(s) have been replaced while retaining the desired biological activities and stability. The wording "one or more amino acids" means the number of amino acids which conventional methods such as site-directed mutagenesis can usually add, remove or replace. The polypeptides containing any one of SEQ ID NOs:6–14 possess both stability and biological activities significantly higher than those of the wild-type polypeptides.

The present polypeptides can be produced by recombinant DNA techniques of: transforming appropriate host cells with DNAs encoding the present polypeptides to obtain a cell containing the DNAs, culturing the cells containing the DNAs to produce the polypeptides, and collecting the produced polypeptides from the resulting culture. The present invention additionally provides a process using the recombinant DNA techniques for producing the present polypeptides, by which the present polypeptides can be easily obtained in a desired amount.

The DNAs used in the present process include all of the DNAs encoding any one of the present polypeptides, which can be obtained by a method of either artificial mutagenesis of DNAs from natural sources or chemical synthesis. An example of the former method is as follows: preparing a DNA with the nucleotide sequence of SEQ ID NO:25 or 28 encoding the amino acid sequence of SEQ ID NO:4 or 5, respectively, from a natural cell as a source, and then applying "overlap extension", a method reported in Robert M. Horton et al. *Methods in Enzymology*, Vol. 217 (New York: Academic Press, Inc., 1993), pp. 270–279, to the DNA to replace one or more codons for the cysteines in SEQ ID NO:4 or 5 with codon(s) for different amino acid(s). The present DNAs include DNAs containing any one of the nucleotide sequence of SEQ ID NOs:15–21, derived from SEQ ID NO:25, SEQ ID NOs:22 and 23, derived from SEQ ID NO:28, the complementary nucleotide sequences to SEQ ID NOs:15–23, and others derived from these nucleotide sequences by replacing one or more of the nucleotides with different one(s) without altering the amino acid sequences encoded thereby. An example of the latter method is chemical synthesis, by which the present DNAs are obtainable in usual manner based on the nucleotide sequences of SEQ ID NOs:9–15. Once obtained by any method, the present DNAs can be easily amplified to a desired amount by using PCR.

Generally in this field, when allowing a DNA encoding a polypeptide to express in a host cell, to improve the expressing efficiency or the biological activities of the polypeptide expressed, one or more nucleotides in the DNA can be replaced with different ones, and an appropriate promoter(s) and/or enhancer(s) can be linked to the DNA. The present DNAs can be also altered similarly as such. For example, nucleotide sequences for recognition sites by appropriate restriction enzymes, initiation codons, termination codons, and/or appropriate signal peptides including the signal peptide of the subtype α2b of interferon-α, shown in SEQ ID NO:16, can be arbitrary linked to the 5'- and/or 3'-termini of any of the nucleotide sequences of SEQ ID NOs:9–15, unless the resulting polypeptides diminish the desired biological activities and stabilities.

The present DNAs can express the present polypeptides with improved stabilities and biological activities after introduced into appropriate host cells from microbial, vegetal, or animal origin, preferably, animal origin. The present DNAs can be introduced into the host cells in the form of recombinant DNAs. The recombinant DNAs usually comprise one of the present DNAs and one of autonomously replicable vectors, which are obtainable by conventional recombinant DNA techniques, once the present DNAs are obtained. Embodiments of the vectors into which the present DNAs can be inserted are plasmid vectors including pCD, pCDL-SRα, pKY4, pCDM8, pCEV4 and pME18S, which usually comprise nucleotide sequences suitable for expressing the present DNAs in hosts, e.g., promoters, enhancers, replication origins, terminators of transcription, splicing sequences, and/or selection markers. The use of vectors with a promotor such as a heat shock protein promotor or the interferon-α promotor disclosed by the present applicant in Japanese Patent Kokai No. 163,368, enables to regulate the present DNAs expression in the transformats by external stimuli.

To insert the present DNAs into the vectors, any conventional method in this field can be used. For example, DNAs containing the present DNAs and the vectors as above are digested by restriction enzymes and/or ultrasonication before the resulting fragments from the present DNAs are ligated with the vector fragments. Digestion by the restriction enzymes, which act on specific nucleotides, preferably, AccI, BamHI, BglII, BstXI, EcoRI, HindIII, NotI, PstI, SacI, SalI, SmaI, SpeI, XbaI, XhoI, etc., facilitate to ligate the DNA fragments with the vector fragments. When ligating the DNA fragments with the vector fragments, they are, if necessary, first annealed, and then treated with a DNA ligase in vivo or in vitro. The recombinant DNAs thus obtained can be unlimitedly replicated in hosts from microbial or animal origin.

The recombinant DNAs can be introduced into host cells suitable to produce the present polypeptides. Whereas any cells conventionally used as host cells in this field can be used in the present invention, the host cells from yeast or mammalian origin are more preferable when the polypeptides produced are used for pharmaceuticals. Embodiments of the host cells from mammalian origin are epithelial, interstitial, and hemopoietic cells from human, monkey, mouse, and hamster, which include 3T3 cells, C127 cells, CHO cells, CV-1 cells, COS cells, HeLa cells, MOP cells, and their mutants. To introduce the present DNAs into the hosts, any conventional methods can be used, e.g., DEAE-dextran method, calcium phosphate transfection method, electroporation method, lipofection method, microinjection method, and viral infection method as using retrovirus, adenovirus, herpesvirus, and vaccinia virus, etc. To select clones producing the present polypeptides from the transformants, the transformants can be cultured before examining the resulting cultures for the present polypeptides produced. The recombinant DNA techniques using mammalian host cells are detailed in publications such as Toshio KUROKI, Masaru TANIGUCHI and Mitsuo OSHIMURA eds., *Jikken-Igaku-Bessatsu, Saibo-Kogaku Handbook* (The handbook for the cell engineering), (Tokyo, Japan: Yodosha. Co., Ltd., 1992), and Takashi YOKOTA and Kenichi ARAI eds., *Jikken-Igaku-Bessatsu, Biomanual Series* 3, *Idenshi-Cloning-Jikken-Ho* (The experimental methods for the gene cloning), (Tokyo, Japan: Yodosha Co., Ltd., 1993).

The transformants thus obtained, cells containing the present DNAs, can produce the present polypeptides intracellularly and/or extracellularly when cultured in culture media. For the culture media, any conventional ones used for transformants can be used. The culture media generally comprise: buffers as a base; inorganic ions such as sodium ion, potassium ion, calcium ion, phosphoric ion, and chloric ion; micronutrients, carbon sources, nitrogen sources, amino acids and vitamins, which can be used depending on metabolic abilities of the cells; and sera, hormones, cell growth factors, and cell adhesion factors, which are used if necessary. Examples of the culture media are 199 medium, DMEM medium, Ham's F12 medium, IMDM medium, MCDB 104 medium, MCDB 153 medium, MEM medium, RD medium, RITC 80-7 medium, RPMI-1630 medium, RPMI-1640 medium, and WAJC 404 medium. Culturing the present transformants under the following conditions can generate cultures containing the present polypeptides: inoculating the present transformants into the culture media to give a cell density of $1\times10^4$–$1\times10^7$ cells/ml, more preferably, $1\times10^5$–$1\times10^6$ cells/ml, and culturing the cells in suspension- or monolayer-cultures at about 37° C. for 1–7 days, more preferably, 2–4 days, if necessary, while replacing the culture media with fresh ones. The cultures thus obtained usually contain the present polypeptides in a concentration of about 1–100 μg/ml, which may vary depending on the types of the transformants or culture conditions used.

While the cultures thus obtained can be used intact as an IFN-γ inducer, they can be usually subjected to the steps for purifying the present polypeptides before use, following the steps of separating the present polypeptides from the cells or the cell debris by filtration, centrifugation, etc., and, if necessary, which may follow a step for disrupting the cells by ultrasonication, cell-lytic enzymes, and/or detergents. To purify the present polypeptides, conventional techniques in this field for purifying biologically active polypeptides can be arbitrary used, e.g., salting-out, dialysis, filtration, concentration, fractional precipitation, ion-exchange chromatography, gel filtration chromatography, adsorption chromatography, isoelectric focusing chromatography, hydrophobic chromatography, reversed phase chromatography, affinity chromatography, gel electrophoresis and/or isoelectric focusing gel electrophoresis. The present polypeptides thus purified can be concentrated and/or lyophilized into liquids or solids depending on final uses. The monoclonal antibodies disclosed in Japanese Patent Application No. 58,240/95 by the present applicant are extremely useful to purify the present polypeptides. Immunoaffinity chromatography using the antibodies can minimize the costs and the labors for obtaining the present polypeptides with a relatively high purity.

The present polypeptides can be usually added to media for culturing immunocompetent cells to produce INF-γ, or administered to humans to treat or prevent INF-γ susceptive diseases. In the case of producing IFN-γ, lymphocytes separated from mammalian peripheral bloods or established cell lines such as HBL-38 cells, Mo cells ATCC CRL8066, Jurkat cells ATCC CRL8163, HuT78 cells ATCC TIB161, EL4 cells ATCC TUB39, L12-R4 cells, and mutant strains thereof are suspended in culture media containing 0.1 ng–1 μg/ml, preferably, 1–100 ng/ml of the present polypeptides. Then, the cells are cultured by conventional methods for about 1–100 hours, if necessary, in the presence of T-cell stimulating agents such as mitogens, interleukin 2, and anti-CD3 antibodies, and while replacing the culture media with fresh ones. To collect the IFN-γ produced, the resulting cultures can be subjected to technique(s) appropriately selected from those conventional for purifying INF-γ, e.g., salting-out, dialysis, filtration, concentration, fractional precipitation, gel filtration chromatography, ion-exchange chromatography, hydrophobic chromatography, adsorption chromatography, affinity chromatography, isoelectric focusing chromatography, gel electrophoresis, and isoelectric focusing gel electrophoresis, etc.

Since the present polypeptides induce production of IFN-γ, agents for susceptive diseases containing the present polypeptides as an effective ingredient can induce production of IFN-γ in human bodies when administered to human, and can treat and/or prevent IFN-γ-susceptive diseases. When the present polypeptides have activities of enhancing cytotoxicities and/or inducing formation of killer cells such as NK cells, LAK cells (lymphokine-activated killer cells), and cytotoxic T cells, besides the IFN-γ inducing activity, as in Examples of the present invention, described below, the killer cells are also involved in treating and/or preventing susceptive diseases. Thus, the wording "susceptive diseases" as referred to in the present invention includes all of the diseases which can be treated and/or prevented by the direct or indirect action of IFN-γ and/or killer cells. The susceptive diseases are viral diseases including hepatitis, herpes, condyloma, and AIDS; infections including candidiasis, malaria, cryptococcoses, diseases caused by Yersinia infection, and tuberculosis; solid malignant tumors including renal carcinoma, mycosis fungoides, and chronic granulomatous diseases; blood-cell-derived malignant tumors including adult T cell leukemia, chronic myelogenous leukemia, and malignant lymphoma; immunopathies including allergies, rheumatism, and collagen diseases; and osteoporosis, etc. The present agents additionally containing interleukin 3 can completely treat or remit leukopenia and thrombopenia caused by radiation therapy or chemotherapy in treating malignant tumors, in addition to leukemia and myeloma.

Thus the present agents for susceptive diseases can be widely used for treating and/or preventing the aforesaid susceptive diseases in the forms of an antitumor agent, an antiviral agent, an antiseptic, an anti-immunopathic agent, a platelet-proliferating agent, and a leukocyte-proliferating agent, etc. The present agents can be usually processed into a liquid, paste, or solid form, containing 0.000001–100 w/w %, preferably, 0.0001–0.1 w/w % of the present polypeptides on a dry solid basis, while the form and the contents may vary depending on the uses and on the types and the symptoms of diseases to be treated and/or prevented.

The present agents can contain not only the present polypeptides solely but also other physiologically acceptable agents to form compositions, e.g., carriers, excipients, diluents, biological response modifiers and stabilizers, and if necessary, one or more other biologically active substances. The stabilizers can be proteins including serum albumins, and gelatins, saccharides including glucose, fructose, sucrose, maltose, lactose, trehalose, sorbitol, mannitol, maltitol, and lactitol, and buffers with phosphoric acid and/or succinic acid. Embodiments of the other biologically active substances are interferon-α, interferon-β, interferon-γ, interleukin 2, interleukin 3, interleukin 12, TNF-α, TNF-β, granulocyte-colony stimulating factor, granulocyte macrophage-colony stimulating factor, carboquone, cyclophosphamide, aclarubicin, thiotepa, busulfan, anbitabine, cytarabine, 5-fluorouracil, 5-fluoro-1-(tetrahydro-2-furyl)uracil, methotrexate, actinomycin D, chromomycin A3, daunorubicin, doxorubicin, bleomycin, mitomycin C, vincristine, vinblastine, L-asparaginase, radio gold colloidal, Krestin®, picibanil, lentinan, and Maruyama vaccine.

Among the above agents, those containing interleukin 2 are particularly useful because the interleukin 2 effects as a cofactor when the present polypeptides induce production of IFN-γ by immunocompetent cells. Thus the agents, additionally containing a natural or recombinant interleukin 2, can induce production of IFN-γ in a desired level by even immunocompetent cells that scarcely produce IFN-γ by the single action of present polypeptides.

The present agents additionally containing interleukin 12 can induce IFN-γ in a particularly high level which the present polypeptides or interleukin 12 per se cannot achieve. In addition, since the present polypeptides can enhance the inhibitory action of interleukin 12 on production of immunoglobulin E antibodies, the present agents with interleukin 12 are useful as an anti-immunopathic agent to treat and/or prevent atopic diseases such as atopic asthma, atopic bronchial asthma, hay fever, allergic rhinitis, atopic dermatitis, vascular edema, and atopic dyspepsia. Because there occasionally exists interleukin 12 in human bodies while in a relatively-low level, then the present polypeptides can achieve the desired effects in the human bodies alone.

The present agents include those in a unit of dose form, which means a physically separated and formed medicament suitable for administration, and contains the polypeptides required for a daily dose or in a dose from 1/40 to several folds (up to 4 folds) of the daily dose. Embodiments of such medicaments are injections, liquids, powders, granules, tablets, capsules, sublinguals, ophthalmic solutions, nasal drops and suppositories.

The present agents can be used for administering orally or parenterally to patients and for activating antitumor cells in vitro as described below, both of which effect to treat and/or prevent the susceptive diseases. For example, the present agents are usually administered orally to patients or parenterally to patients' intradermal tissues, subcutaneous tissues, muscles or veins as observing the patients' symptoms and recuperations at a dose in the range of about 0.1–50 mg/shot, preferably, one μg/shot to one mg/shot of the present polypeptides 1–4 times/day or 1–5 times/week for one day or one year.

The present agents can be also useful in so called "antitumor immunotherapies" using interleukin 2. The antitumor immunotherapies are generally classified into (i) a method administering the interleukin 2 directly to the bodies of patients with malignant tumors, and (ii) a method introducing antitumor cells activated by the interleukin 2 ex vivo to the patients (adoptive immunotherapy), any of which can exert significantly improved effects when used with the present polypeptides. For example, in the method (i), the present polypeptides can be administered to patients at an dose ranging from about 0.1 μg/shot/adult to one mg/shot/adult one to ten times simultaneously with or before the interleukin 2 administration. The dose of interleukin 2, which may vary depending on the types of the malignant tumors, the patients' symptoms and the dose of the present polypeptides, is usually in the range of 10,000–1,000,000 units/shot/adult. In the method (ii), to the media for culturing mononuclear cells or lymphocytes collected from patients with malignant tumors in the presence of the interleukin 2, the present polypeptides can be usually added with an amount of about 0.1 ng–1 μg per $1\times10^6$ of the cell. After the cells are cultured for a prescribed period of time, NK cells or LAK cells are collected from the resulting cultures to be returned to the patients' bodies. Diseases as targets for the present antitumor immunotherapies are: solid malignant tumors such as colonic cancer, rectal cancer, gastric cancer, thyroid carcinoma, cancer of tongues, bladder carcinoma, choriocarcinoma, hepatoma, prostatic cancer, carcinoma uteri, laryngeal, lung cancer, breast cancer, malignant melanoma, Kaposi's sarcoma, cerebral tumor, neuroblastoma, tumor of ovaries, testicular tumor, osteosarcoma, cancer of pancreas, renal cancer, hypernephroma, and hemangioendothelioma; and blood cell malignant tumors such as leukemia and malignant lymphoma, etc.

The present DNAs, encoding the present polypeptides, are also useful in so called "gene therapies". According to conventional techniques in the gene therapies, the present DNAs can be introduced into patients with IFN-γ- and/or killer cell-susceptive diseases by direct injection after inserted into vectors derived from viruses such as retrovirus, adenovirus and adeno-associated virus, or after incorporated into cationic- or membrane fusible-liposomes. Alternatively, the present DNAs can be introduced into the patients by self-transplanting lymphocytes which have been collected from the patients before the DNAs have been introduced into. In adoptive immunotherapies with the gene therapies, the present DNAs can be introduced into effector cells similarly as using the conventional techniques. This can enhance cytotoxicities of the effector cells to tumor cells, resulting in improvement of the adoptive immunotherapy. In tumor vaccine therapy with the gene therapies, tumor cells from patients, into which the present DNAs can be introduced similarly as above, are self-transplanted after proliferated ex vivo up to give a desired cell number. The transplanted tumor cells act as vaccines in the patients to exert a improved antitumor immunity specific to the antigens. Thus the present DNAs exhibit remarkable effects in the gene therapies for diseases including viral diseases, microbial diseases, malignant tumors, and immunopathies. General procedures for the gene therapies are detailed in Takashi SHIMADA, Izumi SAITO and Keiya OZAWA eds., *Jikken-Igaku-Bessatsu, Biomanual UP Series, Idenshich-iryo-no-Kisogijutsu* (Basic techniques for the gene therapy), (Tokyo, Japan: Yodosha Co., Ltd., 1996).

The following examples explain the present invention: Examples A-1 to A-9 describe preferred embodiments of the polypeptides and the process for producing thereof according to the present invention, and Examples B-1 to B-5 describe the preferred embodiments of the agents for susceptive diseases according to the present invention. The techniques in Examples A-1 to A-9 are conventional ones used in this field, which are detailed in publications, e.g., Toshio KUROKI, Masaru TANIGUCHI and Mitsuo OSHIMURA eds., *Jikken-Igaku-Bessatsu, Saibo-Kogaku Handbook* (The handbook for the cell engineering), (Tokyo, Japan: Yodosha. Co., Ltd., 1992), and Takashi YOKOTA and Kenichi ARAI eds., *Jikken-Igaku-Bessatsu, Biomanual Series 3, Idenshi-Cloning-Jikken-Ho* (The experimental methods for the gene cloning), (Tokyo, Japan: Yodosha Co., Ltd., 1993).

EXAMPLE A-1

Production of Polypeptide

EXAMPLE A-1(a)

Construction of Recombinant DNA

Genomic DNA was collected by conventional manner from BALL-1 cells, RCB0256, an established cell line derived from human acute lymphocytic leukemia, and oligonucleotides with the nucleotide sequences of 5' ACAC-CTCGAGCCACCATGGCCTTGACCTTTGCTT TAAC-3' (SEQ ID NO:31) as a sense primer (the sense primer 1) and of 5'-TTGCCAAAGTAGCCCACAGAGCAGCTTG-3' (SEQ ID NO:32) as an antisense primer (the antisense primer 1) were chemically synthesized based on the nucleotide sequence for the signal peptide of the subtype a2b of human interferon-a, shown in SEQ ID NO:24, described in K. Henco et al. *Journal of Molecular Biology*, Vol. 185, pp. 227–260 (1985) . In a 0.5 ml-reaction tube, one ~g of the genomic DNA, lO' ul of 10×PCR buffer, one ~ul of 25 mM dNTP mix, and adequate amounts of the sense primer 1 and the antisense primer 1 were mixed, and sterilized distilled water was added to the mixture to give a volume of 99 p1. To the mixture, one p1 of 2.5 units/pi Pfu DNA polymerase was further added. The mixture was subjected to 30 cycles of incubations at 94° C., 60° C., and 72° C. for one minute, respectively, to perform a PCR, resulting in obtaining a DNA fragment (the DNA fragment 1) which comprised the nucleotide sequence of SEQ ID NO:24, a site recognized by a restriction enzyme of XhoI, linked to the 5'-terminus of the SEQ ID NO:24, and a sequence of 1st–11th nucleotides in SEQ ID NO:25, linked to the 3'-terminus of the SEQ ID NO:24.

The recombinant DNA "pHIGIF", containing the nucleotide sequence of SEQ ID NO:25 encoding the wild-type polypeptide with the amino acid sequence of SEQ ID NO:4, was prepared according to the methods described in Japanese Patent Kokai No. 193,098/96 by the present applicant The wild type polypeptide, with the amino acid sequence of SEQ ID NO:4, contains partial amino acid sequences of SEQ ID NOs:1–3 in the regions of 16th–21st, 30th–35th, and 51st–55th amino acids. Oligonucleotides with the nucleotide sequences of 5' CTGCTCTGTGGGCTACTTTG-GCAAGCTTGAATC-3' (SEQ ID N:33) as a sense primer (the sense primer 2) and 5'-ACACGCGGCCGCCTAGTCT-TCGTTTTG AACAG-3' (SEQ ID NO:34) as an antisense primer (the antisense primer 2) were chemically synthesized in usual manner based on SEQ ID NOs:25 and 26. In a 0.5 ml-reaction tube, one ng of the recombinant DNA "pHIGIF", 10 μl of 10×PCR buffer, one μl of 25 mM dNTP mix and adequate amounts of the sense primer 2 and the antisense primer 2 were mixed, and then sterilized distilled water was added to the mixture to give a volume of 99 μl. To the mixture, one μl of 2.5 units/ μl Pfu DNA polymerase was further added. The mixture was subjected to 30 cycles of incubations at 94° C., 60° C. and 72° C. for one minute, respectively, to perform a PCR, resulting in obtaining a DNA fragment (the DNA fragment 2) which comprised the nucleotide sequence of SEQ ID NO:25, a termination codon of 5'-TAG-3' and a site recognized by a restriction enzyme of NotI, linked to the 5'-terminus of the SEQ ID NO:25, and a sequence of 57th–69th nucleotides in SEQ ID NO:24, linked to the 3' terminus of the SEQ ID NO:25.

In a 0.5 ml-reaction tube, one ng of the DNA fragments 1 and 2 each, 10 μl of 10×PCR buffer, and one μl of 25 mM dNTP mix were mixed, and sterilized distilled water was added to the mixture to give a volume of 99 μl. The mixture was incubated at 94° C. for 3 minutes and slowly cooled to 37° C., and incubated at the temperature for 15 minutes. The mixture was given one μl of 2.5 units/μl Pfu DNA polymerase and slowly heated to 72° C., and then incubated at the temperature for 2 minutes. After added adequate amounts of the sense primer 1 and the antisense primer 2, the mixture was subjected to 30 cycles of incubations at 94° C. for one minute, at 60° C. for one minute, and at 72° C. for 30 seconds, to perform a PCR, resulting in obtaining a DNA fragment (the DNA fragment 3) which comprised the nucleotide sequence of SEQ ID NO:26.

An oligonucleotide with the nucleotide sequence of 5'CTCTGTGAAGTCTGAGAAAATTTCAACTCB-3' (SEQ ID NO:35), as a mutagenic sense primer to replace the 283rd nucleotide of guanine in SEQ ID NO:26 with a cytosine, was chemically synthesized by usual manner. A POR was performed similarly as that for obtaining the DNA fragment 1, but using the DNA fragment 3 as a template and the mutagenic sense primer for the sense primer 1. The PCR resulted in obtaining a DNA fragment (the DNA fragment 4) which comprised a nucleotides sequence identical to 276th–570th nucleotides in SEQ ID NO:26 except for the 287th nucleotide replaced with a cytosine.

An oligonucleotide with the nucleotide sequence of 5'GAGTTGAAATTTTCTCAGACTTCACAGAG-3' (SEQ ID NO:36), as a mutagenic antisense primer to replace the 287th nucleotide of guanine in SEQ ID NO:26 with a cytosine, was chemically synthesized by usual manner. A PCR was performed similarly as that for obtaining the DNA fragment 2, but using the DNA fragment 3 as a template and the mutagenic antisense primer for the antisense primer 1. The PCR resulted in obtaining a DNA fragment (the DNA fragment 5) which comprised a nucleotides sequence identical to 1st–304th nucleotides in SEQ ID NO:26 except for the 287th nucleotide replaced with a cytosine.

A PCR was performed similarly as that for obtaining the DNA fragment 3, but using the DNA fragments 4 and 5 as templates, to obtain a DNA fragment (the DNA fragment 6) containing a nucleotide sequence encoding the amino acid sequence of SEQ ID NO:6. The DNA fragment 6 comprised the nucleotide sequence of SEQ ID NO:15, the nucleotide sequence of SEQ ID NO:24 and a site recognized by a restriction enzyme XhoI, linked to the 5'-terminus of the SEQ ID NO:15, and a termination codon of the nucleotides of 5'-TAG-3' and a site recognized by a restriction enzyme NotI, linked to 3'-terminus of the SEQ ID NO:15.

After the DNA fragment 6 by restriction enzymes XhoI and NotI was cleaved to generate a DNA fragment of 555 bps, 25 ng of the generated DNA fragment was mixed with 10 ng of a plasmid vector "pCDM8", commercialized by Invitrogen Corporation, San Diego, USA, which had been cleaved by the XhoI and NotI, and then the mixture was incubated at 16° C. for 30 minutes using a ligation kit "LIGATION KIT VERSION 2", commercialized by Takara Shuzo Co., Tokyo, Japan. By cloning, an autonomously replicable recombinant DNA "pCSHIGIF/MUT12" consisting of 4,494 bp was obtained. As shown in FIG. 1, in the recombinant DNA "pCSHIGIF/MUT12", a cDNA "IGIF/MUT12" with the nucleotide sequence of SEQ ID NO:15 was linked to downstream of the nucleotide sequence "IFNss", encoding the signal peptide of the subtype α2b of human interferon-α. As shown in the accompanied amino acid sequence, the nucleotide sequence of SEQ ID NO:15 encodes the amino acid sequence of SEQ ID NO:6, derived from the wild-type polypeptide with SEQ ID NO:4 by replacing the cysteine at the 68th position.

Figure 2:
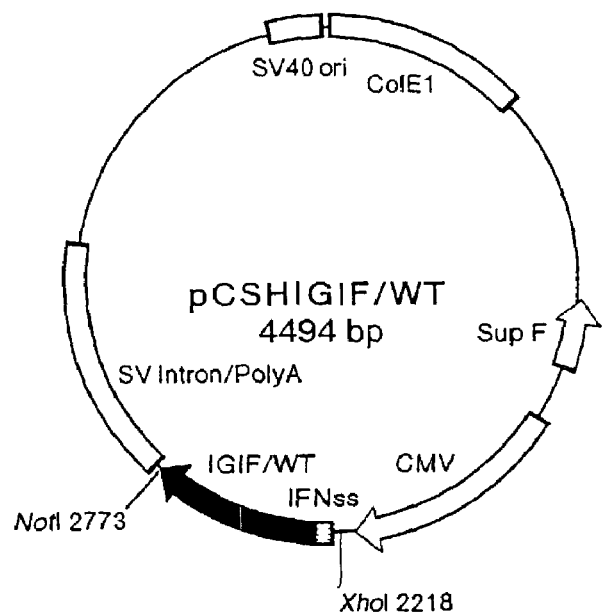
FIG. 2 is the restriction map of a recombinant DNA "pCSHIGIF/WT" encoding the wild-type polypeptide from human origin.

For a control, an autonomously replicable recombinant DNA "pCSHIGIF/WT" was prepared similarly as above excepting the DNA fragment 6 replaced with the DNA fragment 3. As shown in FIG. 2, in the recombinant DNA "pCSHIGIF/WT", a cDNA "IGIF/WT" with the nucleotide sequence of SEQ ID NO:25, encoding the wild-type polypeptide, was linked to downstream of the nucleotide sequence "IFNss", encoding the signal peptide of subtype α2b of human interferon-α.

EXAMPLE A-1(b)

Production of Polypeptide by Transformant

The recombinant DNA "pCSHIGIF/MUT12", obtained in Example A-1(a), was introduced by conventional competent-cell method into an *Escherichia coli* strain "MC1061/P3", commercialized by Invitrogen Corporation, San Diego, USA, to obtain a transformant. The transformant was cultured in L medium (pH 7.2) containing 20 μg/ml ampicillin and 10 μg/ml tetracycline at 37° C. for 18 hours under shaking conditions. The resulting culture was centrifuged to separate the cells, and the separated cells were subjected to conventional alkali-SDS method to extract the recombinant DNA.

2.5 ml of DME medium (pH 7.4) supplemented with 10 v/v % fetal bovine serum was put into each well of six-well microplates, and $1.8\times10^5$ cells of COS-1, ATCC CRL1650, an established cell line derived from African green monkey kidney, was inoculated into each well. The microplates were incubated at 37° C. for 24 hours in a 5 v/v % $CO_2$ incubator. After the incubation, the media were removed, and the wells were washed with DME medium containing 50 mM Tris-HCl buffer (pH 7.4). To each well, 1.8 ml of DME medium containing 2.8 μg/ml of the recombinant DNA obtained above, 50 mM Tris-HCl buffer (pH 7.4), 0.4 mg/ml DEAE-dextran and 0.1 mM chloroquine was added, and the microplates were incubated at 37° C. for 4 hours in a 5 v/v % $CO_2$ incubator. After the incubation, the media were removed, and 2.5 ml of 10 mM phosphate buffer (pH 7.4) containing 10 v/v % dimethylsulfoxide and 140 mM NaCl was added to each well, and then the microplates were stood at ambient temperature for 2 minutes. After the standing, the buffers were removed, and the wells were washed with DME medium containing 50 mM Tris-HCl buffer (pH 7.4). To each well, 2.5 ml of a culture medium "COS MEDIUM", commercialized by COSMOBIO Co., Ltd., Tokyo, Japan, was added, and the microplates were incubated at 37° C. for 3 days in a 5 v/v % $CO_2$ incubator to culture the cells. The resulting culture was analyzed by Western blotting using the monoclonal antibody described in Japanese Patent Kokai No. 231,598/96. The analysis proved that the present polypeptide, capable of inducing production of IFN-γ by immunocompetent cells and containing an amino acid sequence derived from SEQ ID NO:4 by replacing the cysteine at 68th position with a serine, was produced in the culture in an amount of about 20 ng/ml.

As a control experiment, the recombinant DNA "pCSHIGIF/WT" obtained in Experiment A-1(a) was treated similarly as the recombinant DNA "pCSHIGIF/MUT12". Consequently, the wild-type polypeptide capable of inducing production of IFN-γ was produced in the culture in an amount of about one ng/ml. This yield was no more than 5% of that obtained by using the recombinant DNA "pCDHIGIF/MUT12". This indicates that the polypeptide according to the present invention, in this Example, is more stable and exhibits biological activities higher than the wild-type polypeptide.

EXAMPLE A-1(c)

Purification of Polypeptide

The culture containing the present polypeptide that was obtained in Experiment A-1(b) was centrifuged to collect a supernatant. After the supernatant was fed to a column, which was packed with a gel for immunoaffinity chromatography using the monoclonal antibody, prepared according to the methods disclosed in Japanese Patent Kokai No. 231,598/96 by the present applicant, and preliminarily washed with phosphate-buffered saline (hereinafter abbreviated as "PBS"), a fresh PBS was run through the column to wash, and then 0.1 M glycine-HCl buffer (pH 2.5) containing one M NaCl was run to elute. From the eluted fractions, those containing the polypeptide capable of inducing production IFN-γ by immunocompetent cells were collected. The collected fractions were dialyzed against PBS at 4° C. for 18 hours, and then concentrated by membrane-filtration followed by lyophilization to obtain a solid polypeptide with a purity of about 95% or higher and a recovery of about 50% to the culture of the starting material. In parallel, the culture containing the wild-type polypeptide, obtained by using the recombinant DNA "pCSHIGIF/WT", was purified similarly as above for a control in analyzing the physicochemical properties as described below.

EXAMPLE A-1(d)

Molecular Weight

SDS-Polyacrylamide gel electrophoresis of the polypeptide in Example A-1(c) in the presence of 2 w/v % dithiothreitol as a reducing agent, according to the method described in U. K. Laemli, Nature, Vol. 227, pp. 680–685 (1970), exhibited a main band of a protein capable of inducing IFN-γ at a position corresponding to a molecular weight of about 18,000–19,500 daltons. The molecular weight makers used were bovine serum albumin (67,000 daltons), ovalbumin (45,000 daltons), carbonic anhydrase (30,000 daltons), soy bean trypsin inhibitor (20,100 daltons), and α-lactoalbumin (14,000 daltons).

EXAMPLE A-1(e)

N-Terminal Amino Acid Sequence

Conventional analysis using a protein sequencer "MODEL 473A", commercialized by Perkin-Elmer Corp., Norwalk, USA, revealed that the polypeptide in Example A-1(c) had the amino acid sequence of SEQ ID NO:27 in the N-terminal region.

EXAMPLE A-1(f)

Stability

The present polypeptide or the wild-type polypeptide, in Example A-1(c), was dissolved in a culture medium "COS MEDIUM", commercialized by COSMOBIO Co., Ltd., Tokyo, Japan, to give about 10 ng/ml, and the solution was incubated at 40° C. for 24 hours. After 0, 0.5, 1, 2, 4, 6, 8, 12, or 24 hours from starting the incubation, a portion of each solution was sampled. The samples were individually assayed on IFN-γ inducing activity, according to the methods described below, in Example A-1(g), to study the time course of the activity upon the incubation. Percentage (%) of the residual activity at every point was calculated based on the activity at the starting point. The results are in FIG. 3.

Figure 3:
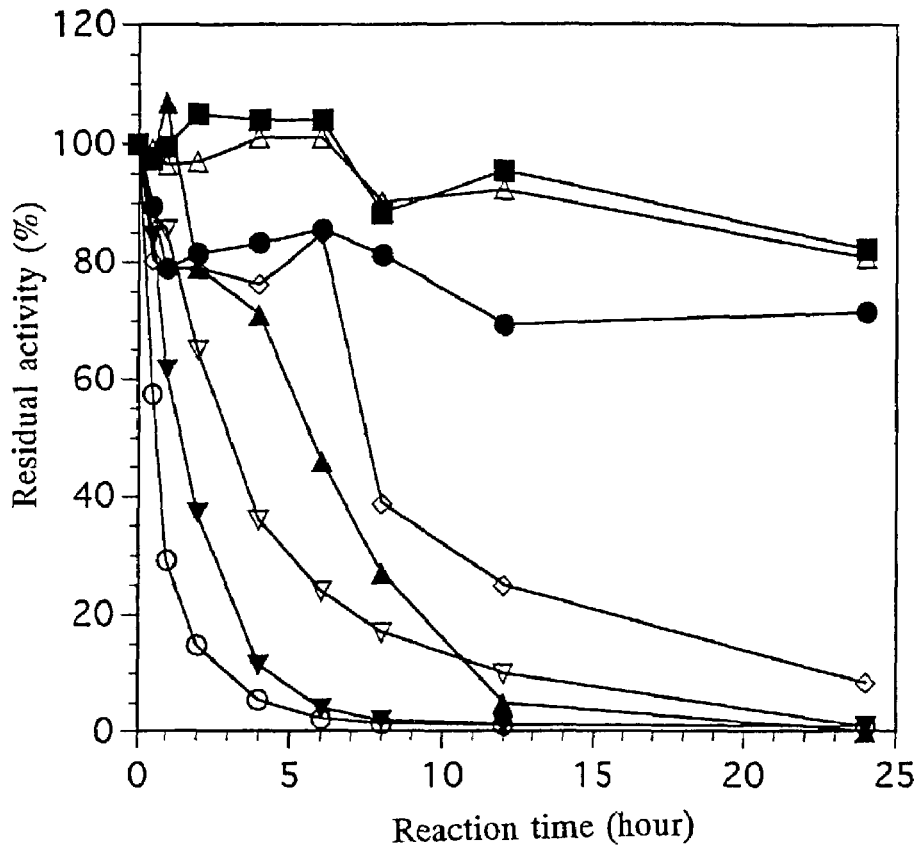
FIG. 3 shows the time course of activity upon incubation of the polypeptides according to the present invention and the wild-type polypeptide, from human origin.

As shown in FIG. 3, the polypeptide in this Example was more stable and retained the activity longer than the wild-type polypeptide. This evidences that the amino acid replacement used in this Example can effectively improve the stability of the wild type polypeptide without reducing the biological activities.

EXAMPLE A-1(g)

Production of IFN-γ by Immunocompetent Cells

KG-1 cells, ATCC CCL246, an established cell line derived from human acute myelogenous leukemia, were inoculated into RPMI-1640 medium (pH 7.4) with no sera to give a density of $3 \times 10^5$ cells/ml and cultured at 37° C. for 4 days in a 5 v/v % $CO_2$ incubator. The cultured cells were collected and suspended to give a density of $3 \times 10^6$ cells/ml in RPMI-1640 medium (pH 7.4) supplemented with 10 v/v % fetal bovine serum. 0.1 ml of the cell suspension was put into each well of 96-well microplates, and 0.1 ml of a solution containing the present polypeptide or the wild-type polypeptide, obtained in Example A-1(c), which had been diluted appropriately, was added to each well. Thereafter, the cells were cultured at 37° C. for 24 hours in a 10 v/v % $CO_2$ incubator. 0.1 ml of supernatants of the cultures were collected from the wells and examined on productions of IFN-γ by conventional enzyme-immunoassay. As a blank, an experiment was taken in parallel identically as above but using no polypeptides. Table 1 shows the results. The productions of IFN-γ in Table 1 were expressed with international units (IU), calculated based on the IFN-γ standard Gg23-901-530, obtained from the International Institute of Health, USA.

TABLE 1

| Polypeptide concentration, ng/ml | Production of IFN-γ, IU/ml* |  |
|---|---|---|
| 0 | 0 | (0) |
| 0.1 | 0.7 | (0.6) |
| 0.2 | 3.0 | (2.4) |
| 0.4 | 8.1 | (7.4) |
| 0.8 | 20.0 | (18.9) |
| 1.0 | 30.0 | (25.9) |

*Value in parentheses represents the production of IFN-γ when using the wild-type polypeptide.

Table 1 indicates that the present polypeptide acted on KG-1, an immunocompetent cell, to induce the production of IFN-γ. The IFN-γ production was equal to or higher than that induced by the wild-type polypeptide.

EXAMPLE A-1(h)

Enhancement of Cytotoxicity of NK Cells

A fresh blood was collected from a healthy donor by using a syringe containing heparin, and the blood was diluted with the equal volume of PBS. The diluted blood was overlaid on FICOLL and centrifuged to obtain high-density lymphocytes. The lymphocytes were suspended to give a density of $1 \times 10^6$ cells/ml in RPMI-1640 medium (pH 7.2) containing 10 μg/ml kanamycin, $5 \times 10^{-5}$ M 2-mercaptoethanol and 10 v/v % fetal bovine serum. 0.5 ml of the cell suspension was put into each well of 12-well microplates. To each well, the present polypeptide or the wild-type polypeptide, obtained in Example A-1(c), in 1.5 ml solution was added after appropriately diluted with a fresh preparation of the medium, and 0.5 ml of a fresh preparation of the medium with or without 50 units/ml of a recombinant human interleukin 2 was further added. Thereafter, the cells were cultured at 37° C. for 24 hours in a 5 v/v % $CO_2$ incubator. The cultured cells were washed with PBS to obtain cultured lymphocytes containing NK cells as effector cells.

K-562 cells, ATCC CCL243, an established cell line derived from human chronic myelogenous leukemia, as target cells sensitive to NK cells, were labelled with $^{51}Cr$ by a conventional method, and $1 \times 10^4$ cells of the labelled cells were put into each well of 96-well microplates. To the wells, the cultured lymphocytes obtained above were added to give the ratios of 2.5:1, 5:1 and 10:1 between the effector and the target cells, before cultured at 37° C. for 4 hours in a 5 v/v % $CO_2$ incubator. Thereafter, the culture supernatants were examined on the radioactivity by conventional manner to estimate the number of killed cells. Percentage (%) of the killed cells to the target cells tested in each system was calculated to evaluate the cytotoxicity. Table 2 shows the results.

TABLE 2

| Concentration of Polypeptide, pM* | Concentration of Interleukin 12, unit/ml | Cytotoxicity, %** [Effector Cells] : [Target Cells] | | |
|---|---|---|---|---|
| | | 2.5:1 | 5:1 | 10:1 |
| 0 | 0 | 22 (22) | 35 (35) | 65 (65) |
| 0 | 10 | 30 (30) | 48 (48) | 73 (73) |
| 0.5 | 0 | 25 (23) | 41 (36) | 65 (66) |
| 0.5 | 10 | 31 (32) | 54 (50) | 69 (75) |
| 5 | 0 | 28 (25) | 49 (39) | 66 (68) |
| 5 | 10 | 36 (35) | 58 (52) | 79 (78) |
| 50 | 0 | 30 (29) | 53 (47) | 77 (73) |
| 50 | 10 | 42 (41) | 62 (59) | 82 (85) |
| 500 | 0 | 33 (37) | 56 (50) | 84 (83) |
| 500 | 10 | 57 (52) | 78 (70) | 96 (93) |

NOTE)
*"pM" means a molarity of $10^{-12}$ M.
**Value in parentheses represents the cytotoxicity exhibited when using the wild-type polypeptide.

As shown in Table 2, the present polypeptide enhanced the cytotoxicity of NK cells, and the enhancement was equal to or higher than that of the wild-type polypeptide. The enhancement was augmented by the co-existing of interleukin 2.

EXAMPLE A-1(i)

Induction of LAK Cell Formation

Cultured lymphocytes containing LAK cells as effector cells were prepared by a procedure similar as in Example A-1(g) excepting the culturing time replaced with 72 hours. Raji cells, ATCC CCL86, an established cell line derived from human Burkitt lymphoma, as target cells non-sensitive to NK cells, was labelled with $^{51}$Cr according to the conventional method. $1\times10^4$ of the labelled cells were put into each well of 96-well microplates, and the cultured lymphocytes were added to the wells to give the ratios of 5:1, 10:1, and 20:1 between the effector and the target cells, before cultured at 37° C. for 4 hours in a 5 v/v % $CO_2$ incubator. Thereafter, similarly as in Example A-1(g), the culture supernatants were examined on the radioactivity to evaluate the cytotoxicity. Table 3 shows the results.

higher than that of the wild-type polypeptide. The induction was augmented by the co-existing of interleukin 2.

EXAMPLE A-1(i)

Acute Toxicity Test

The present polypeptide in Example A-1(c) was percutaneously, perorally or intraperitoneally administered to 8-week-old mice in usual manner. As a result, the $LD_{50}$ of the present polypeptide proved to be about one mg or higher per one kg of the body weight, independently of the administration routs. This evidences that the present polypeptide can be incorporated into pharmaceuticals for humans without anxiety.

EXAMPLE A-2

Production of Polypeptide

An autonomously replicable recombinant DNA "pCSHIGIF/MUT21" containing the nucleotide sequence of SEQ ID NO:16 was obtained by a procedure similar as in Example A-1(a) but using the DNA fragment 6, obtained in

TABLE 3

| Concentration of Polypeptide, pM* | Concentration of Interleukin 12, unit/ml | Cytotoxicity, %** [Effector Cells] : [Target Cells] | | |
|---|---|---|---|---|
| | | 5:1 | 10:1 | 20:1 |
| 0 | 0 | 11 (11) | 21 (21) | 34 (34) |
| 0 | 10 | 15 (15) | 28 (28) | 38 (38) |
| 0.5 | 0 | 14 (13) | 24 (22) | 34 (35) |
| 0.5 | 10 | 18 (17) | 32 (31) | 42 (43) |
| 5 | 0 | 16 (15) | 26 (23) | 37 (39) |
| 5 | 10 | 21 (19) | 36 (34) | 50 (48) |
| 50 | 0 | 22 (20) | 41 (25) | 49 (44) |
| 50 | 10 | 26 (23) | 52 (42) | 56 (54) |
| 500 | 0 | 27 (27) | 44 (34) | 61 (57) |
| 500 | 10 | 33 (31) | 59 (54) | 72 (67) |

NOTE)
*"pM" means a molarity of $10^{-12}$ M.
**Value in parentheses represents the cytotoxicity exhibited when using the wild-type polypeptide.

Figure 4:
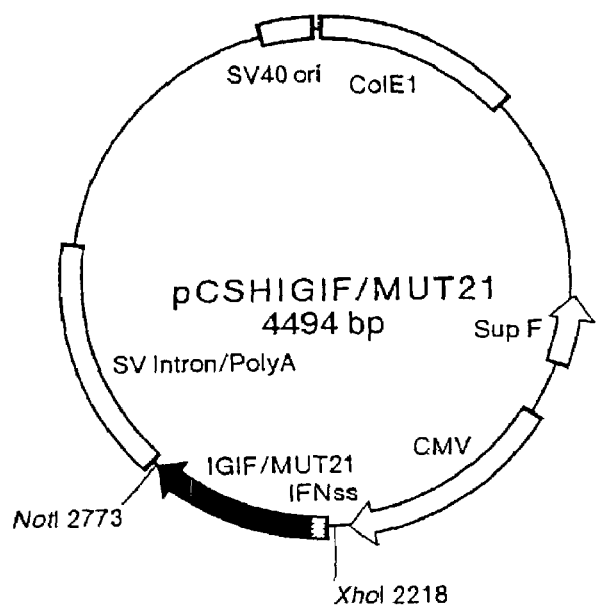
FIG. 4 is the restriction map of a recombinant DNA "pCSHIGIF/MUT21" encoding another polypeptide according to the present invention.

As shown in Table 3, the present polypeptide induced the formation of LAK cells, and the induction was equal to or Example A-1(a), as a template, and an oligonucleotide with the nucleotide sequence of 5'-CTGATTCTGACTCTA- GATAATGC-3' (SEQ ID NQ:37) and an oligonucleotide with the nucleotide sequence of 5'-GCATTATCTCTA-GAGTCAGAATCAG-3' (SEQ ID NO:38), as a mutagenic sense and a mutagenic antisense primer, respectively, to replace the cysteine at 38th position in SEQ ID NO:4 with a serine. As shown in FIG. 4, in the recombinant DNA "pCSHIGIF/MUT21't, a cDNA "IGIF/MUT21" encoding the amino acid sequence of SEQ ID NO:7 was linked to downstream of the nucleotide sequence "IFNss", encoding the signal peptide of the subtype α2b of human interferon-α.

The recombinant DNA was introduced into COS-1 cells similarly as in Example A-1(b) to obtain a transformant. Culturing the transformant produced the polypeptide with the amino acid sequence of SEQ ID NO:7 in an amount of about 50 ng per one ml of the culture. The culture was purified before analyzed on the physicochemical properties similarly as in Example A-1. As a result, the polypeptide in this Example proved to be similar to that in Example A-1 in the properties, i.e., the molecular weight, the N-terminal amino acid sequence, and the less toxicity. As shown in FIG. 3, the results of the analysis on stability, obtained according to the method in Example A-1(f), the present, polypeptide in this Example was more stable than the wild-type polypeptide. These results evidence that the amino acid replacement used in this Example can effectively improve the stability of the wild type polypeptide without reducing the biological activities.

EXAMPLE A-3

Production of Polypeptide

Figure 5:
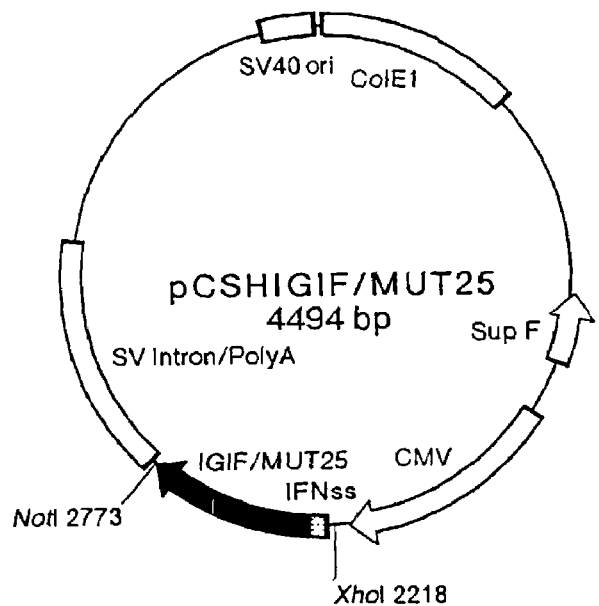
FIG. 5 is the restriction map of a recombinant DNA "pCSHIGIF/MUT25" encoding further another polypeptide according to the present invention.

An autonomously replicable recombinant DNA "pCSHIGIF/MUT25" containing the nucleotide sequence of SEQ ID NO:17 was obtained by a procedure similar as in Example A-1(a) but using the DNA fragment 6, obtained in Example A-1(a), as a template, and an oligonucleotide with the nucleotide sequence of 5'-CTTTCTAGCTTCT-GAAAAAGAGAGAG-3' (SEQ ID NO:39) and an oligonucleotide with the nucleotide sequence of 5'-CTCTCTCTTTTTCAGAAGCTAGAAAG-3' (SEQ ID NO:40), as a mutagenic sense and a mutagenic antisense primer, respectively, to replace the cysteine at 127th position in SEQ ID NO:4 with a serine. As. shown in FIG. 5, in the recombinant DNA "pCSHIGIF/MUT25", a cDNA "IGIF/MUT25" encoding the amino acid sequence of SEQ ID NO:8 was linked to downstream of the nucleotide sequence "IFNss", encoding the signal peptide of the subtype α2b of human interferon-α.

The recombinant DNA was introduced into COS-1 cells similarly as in Example A-1(b) to obtain a transformant. Culturing the transformant produced the polypeptide with the amino acid sequence of SEQ ID NO:4 in an amount of about 30 ng per one ml of the culture. The culture was purified before analyzed on the physicochemical properties similarly as in Example A-1. As a result, the polypeptide in this Example proved to be similar to that in Example A-1 in the properties, i.e., the molecular weight, the N-terminal amino acid sequence, and the less toxicity. As shown in FIG. 3, the results of the analysis on stability, obtained according to the method in Example A-1(f), the present polypeptide in this Example was more stable than the wild-type polypeptide. These results evidence that the amino acid replacement used in this Example can effectively improve the stability of the wild type polypeptide without reducing the biological activities.

EXAMPLE A-4

Production of Polypeptide

Figure 6:
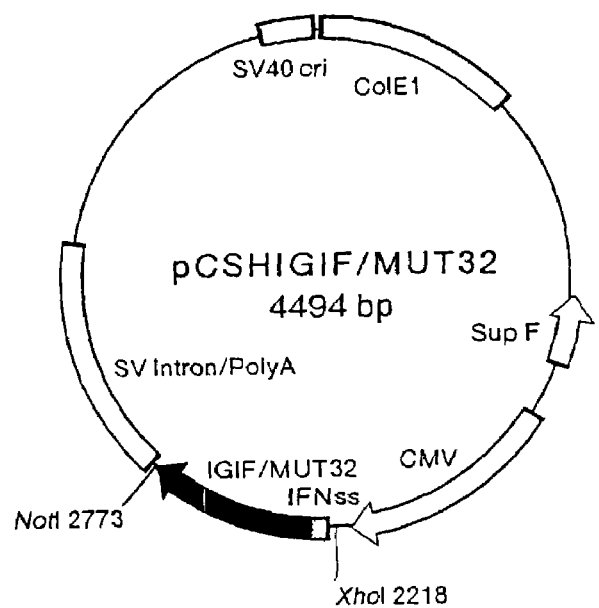
FIG. 6 is the restriction map of a recombinant DNA "pCSHIGIF/MUT32" encoding further another polypeptide according to the present invention.

An autonomously replicable recombinant DNA "pCSHIGIF/MUT32" containing the nucleotide sequence of SEQ ID NO:18 was obtained by a procedure similar as in Example A-1(a) but using the cDNA "IGIF/MUT21" as a template, encoding the amino acid sequence of SEQ ID NO:7, in the recombinant DNA "pCSHIGIF/MUT21" obtained in Example A-2, and an oligonucleotide with the nucleotide sequence of 5'-CTTTCTAGCTTCTGAAAAA-GAGAGAG-3' (SEQ ID NO:39) and an oligonucleotide with the nucleotide sequence of 5'CTCTCTCTTTTCA-CAAGCTAGAAAG-3' (SEQ ID No:40), as a mutagenic sense and a mutagenic antisense primer, respectively, to replace the cysteine at 127th position in SEQ ID NO:4 with a serine. As shown in FIG. 6, in the recombinant DNA "pCSHIGIF/MUT32", a cDNA "IGIF/MUT32" encoding the amino acid sequence of SEQ ID NO:9 was linked to downstream of the nucleotide sequence "IFNss", encoding the signal peptide of the subtype α2of human interferon-α.

The recombinant DNA was introduced into COS-1 cells similarly as in Example A-1(b) to obtain a transformant. Culturing the transformant produced the polypeptide with the amino acid sequence of SEQ ID NO:9 in an amount of about 80 ng per one ml of the culture. The culture was purified before analyzed on the physicochemical properties similarly as in Example A-1. As a result, the polypeptide in this Example proved to be similar to that in Example A-1 in the properties, i.e., the molecular weight, the N-terminal amino acid sequence, and the less toxicity. As shown in FIG. 3, the results of the analysis on stability, obtained according to the method in Example A-1(f), the present polypeptide in this Example was more stable than the wild-type polypeptide. These results evidence that the amino acid replacement used in this Example can effectively improve the stability of the wild type polypeptide without reducing the biological activities.

EXAMPLE A-5

Production of Polypeptide

Figure 7:
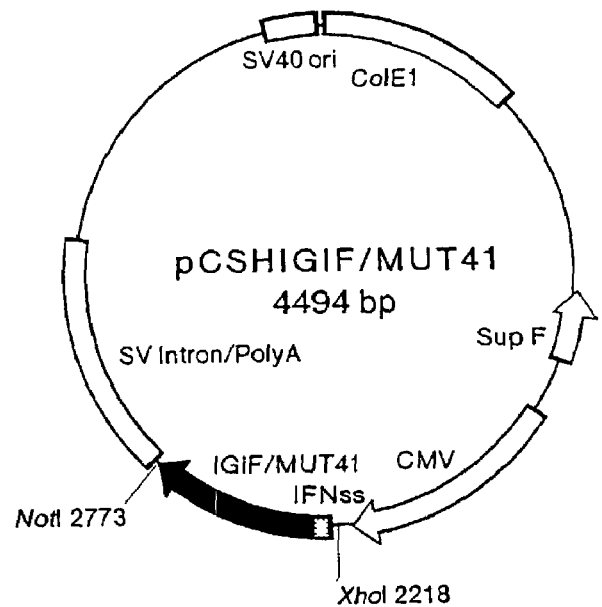
FIG. 7 is the restriction map of a recombinant DNA "pCSHIGIF/MUT41" encoding further another polypeptide according to the present invention.

An autonomously replicablle recombinant DNA "pCSHIGIF/MUT41" containing the nucleotide sequence of SEQ ID NO:19 was obtained by a procedure similar as in Example A-1(a) but using the cDNA "IGIF/MUT32" as a template, with the nucleotide sequence of SEQ ID NO:18, in the recombinant DNA "pCSHIGIF/MUT32" obtained in Example A-4, and an oligonucleotide with the nucleotide sequence of 5'-CAACTCTCTCCTCTGAGAACAA-3' (SEQ ID NO:41) and an oligonucleotide with the nucleotide sequence of 5'TTGTTCTCAGAGGAGAGAGTTG-3' (SEQ ID NO:42), as a mutagenic sense and a mutagenic antisense primer, respectively, to replace the cysteine at 76th position in SEQ ID NO:4 with a serine. As shown in FIG. 7, in the recombinant DNA "pCSHIGIF/MUT41", a cDNA "IGIF/MUT41" encoding the amino acid sequence of SEQ ID NO:10 was linked to downstream of the nucleotide sequence "IFNss", encoding the signal peptide of the subtype α2b of human interferon—α.

The recombinant DNA was introduced into COS-1 cells similarly as in Example A-1(b) to obtain a transformant. Culturing the transformant produced the polypeptide with the amino acid sequence of SEQ ID NO:10 in an amount of about 6 ng per one ml of the culture. The culture was purified before analyzed on the physicochemical properties similarly as in Example A-1. As a result, the polypeptide in this Example proved to be similar to that in Example A-1 in the properties, i.e., the molecular weight, the N-terminal amino acid sequence, and the less toxicity. As shown in FIG. 3, the results of the analysis on stability, obtained according to the method in Example A-1(f), the present polypeptide in this Example was more stable than the wild-type polypeptide. These results evidence that the amino acid replacement used in this Example can effectively improve the stability of the wild type polypeptide without reducing the biological activities.

EXAMPLE A-6

Production of Polypeptide

Figure 8:
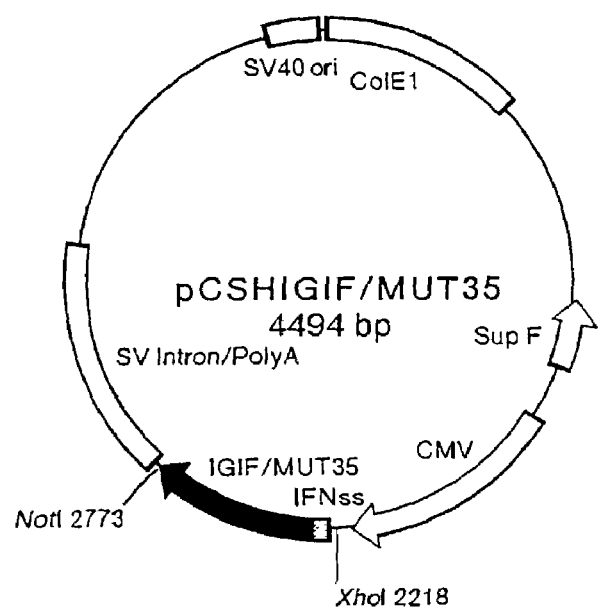
FIG. 8 is the restriction map of a recombinant DNA "pCSHIGIF/MUT35" encoding further another polypeptide according to the present invention.

An autonomously replicable recombinant DNA "pCSHIGIF/MUT35" containing the nucleotide sequence of SEQ ID NO:20 was obtained by a procedure similar as in Example A-1(a) but using the cDNA "IGIF/MUT21" as a template, encoding the amino acid sequence of SEQ ID NO:7, in the recombinant DNA "pCSHIGIF/MCJT21" obtained in Example A-2, and an oligonucleotide. with the nucleotide sequence of 5'-CTCTCCGCTGAGAA-CAAAATTATTTCC3' (SEQ ID NO:43) and an oligonucleotide with the nucleotide sequence of 5'TTTGTTCT-CAGCGGAGAGAGTTG-3' (SEQ ID NO:44), as a mutagenic sense and a mutagenic antisense primer, respectively, to replace the cysteine at 76th position in SEQ ID NO:4 with an alanine. As shown in FIG. 8, in the recombinant DNA "pCSHIGIF/MUT41", a cDNA "IGIF/MUT35" encoding the amino acid sequence of SEQ ID NO:11 was linked to downstream of the nucleotide sequence "IFNss", encoding the signal peptide of the subtype α2b of human interferon-α.

The recombinant DNA was introduced into COS-1 cells similarly as in Example A-1(b) to obtain a transformant. Culturing the transformant produced the polypeptide with the amino acid sequence of SEQ ID NO:11 in an amount of about 60 ng per one ml of the culture. The culture was purified before analyzed on the physicochemical properties similarly as in Example A-1. As a result, the polypeptide in this Example proved to be similar to that in Example A-1 in the properties, i.e., the molecular weight, the N-terminal amino acid sequence, and the less toxicity. As shown in FIG. 3, the results of the analysis on stability, obtained according to the method in Example A-1(f), the present polypeptide in this Example was more stable than the wild-type polypeptide. These results evidence that the amino acid replacement used in this Example can effectively improve the stability of the wild type polypeptide without reducing the biological activities.

EXAMPLE A-7

Production of Polypeptide

Figure 9:
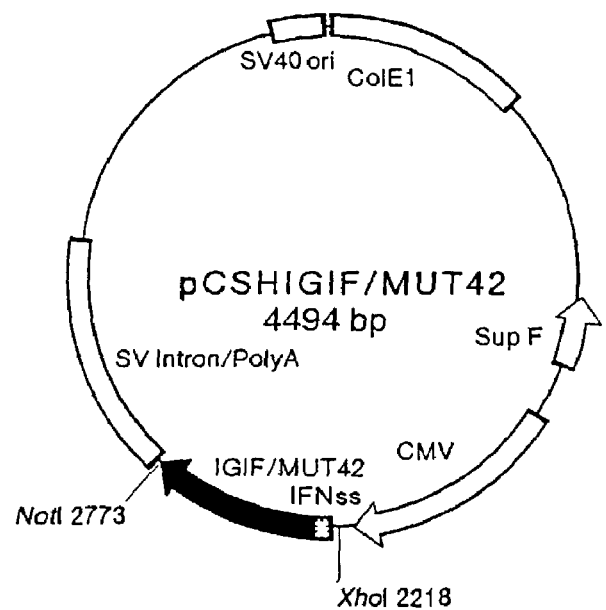
FIG. 9 is the restriction map of a recombinant DNA "pCSHIGIF/MUT42" encoding further another polypeptide according to the present invention.

An autonomously replicable recombinant DNA "pCSHIGTF/MUT42" containing the nucleotide sequence of SEQ ID NO:21 was obtained by a procedure similar as in Example A-1(a) but using the cDNA "IGIF/MUT32" as a template, encoding the amino acid sequence of SEQ ID NO:18, in the recombinant DNA "pCSHIGIF/MUT32" obtained in Example A-4, and an oligonucleotide with the nucleotide sequence of 5'-CTCTCCGCTGAGAA-CAAAATTATTTCC3' (SEQ ID NO:43) and an oligonucleotide with the nucleotide sequence of 5'TTTGTTCT-CAGCGGAGAGAGTTG-3' (SEQ ID NO:44), as a mutagenic sense and a mutagenic antisense primer, respectively, to replace the cysteine at 76th position in SEQ ID NO:4 with an alanine. As shown in FIG. 9, in the recombinant DNA "pCSHIGIF/MUT42", a cDNA "IGIF/MUT42" encoding the amino acid sequence of SEQ ID NO:12 was linked to downstream of the nucleotide sequence "IFNss", encoding the signal peptide of the subtype α2b of human interferon-α.

The recombinant DNA was introduced into COS-1 cells similarly as in Example A-1(b) to obtain a transformant. Culturing the transformant produced the polypeptide with the amino acid sequence of SEQ ID NO:12 in an amount of about 30 ng per one ml of the culture. The culture was purified before analyzed on the physicochemical properties similarly as in Example A-1. As a result, the polypeptide in this Example proved to be similar to that in Example A-1 in the properties, i.e., the molecular weight, the N-terminal amino acid sequence, and the less toxicity. As shown in FIG. 3, the results of the analysis on stability, obtained according to the method in Example A-1(f), the present polypeptide in this Example was more stable than the wild-type polypeptide. These results evidence that the amino acid replacement used in this Example can effectively improve the stability of the wild type polypeptide without reducing the biological activities.

EXAMPLE A-8

Production of Polypeptide

A PCR was performed similarly as the PCR for obtaining the DNA fragment 1 in Example A-1(a) but using an oligonucleotide with the nucleotide sequence of 5'CGGC-CAAAGTTGCCCACAGAGCAGCTTG-3' (SEQ ID NO:45), chemically synthesized, for the antisense primer 1. The PCR resulted in obtaining a DNA fragment (the DNA fragment 7) which comprised the nucleotide sequence of SEQ ID NO:24, a site recognized by a restriction enzyme XhoI, linked to the 5'-terminus of the SEQ ID NO:24, and a sequence of 1st–11th nucleotides in the nucleotide sequence of SEQ ID NO:28, linked to the 3'-terminus of the SEQ ID NO:24.

The recombinant DNA "pMGTG-1", containing the nucleotide sequence of SEQ ID NO:28 encoding the wild-type polypeptide with the amino acid sequence of SEQ ID NO:5, was prepared according to the methods described in Japanese Patent Kokai No. 27,189/96 by the present applicant. The wild type polypeptide, with the amino acid sequence of SEQ ID NO:5, contains partial amino acid sequences of SEQ ID NOs:1, 2 and 3 in the parts consisting of 16th–21st, 29th–34th, and 50th–54th amino acids, respectively. Oligonucleotides with the nucleotide sequence of 5'-CTGCTCTGTGGGCAACTTTGGccGACTTCACTG-3' (SEQ ID NO:46) as a sense primer (the sense primer 3) and 5'ACACGCGGCCGCCTAACTTTGATGTAAGTTAG-3' (SEQ ID NO:47) as an antisense primer (the antisense primer 3) were chemically synthesized. Thereafter, a PCR was performed similarly as that for obtaining the DNA fragment 2 in Example A-1(a) but using the recombinant DNA "pMGTG1", the sense primer 3 and the antisense primer 3 for the recombinant DNA "pHIGIF", the sense primer 2 and the antisense primer 2, respectively. The PCR resulted in obtaining a DNA fragment (the DNA fragment 8) which comprised the nucleotide sequence of SEQ ID NO:28, a termination codon of 5'-TAG-3' and a site recognized by a restriction enzyme NotI, linked to the 3'-terminus of the SEQ ID NO:28, and a sequence of 57th–69th nucleotides in the nucleotide sequence of SEQ ID NO:24, linked to the 5'-terminus of the SEQ ID NO:28.

A PCR was performed similarly as that for obtaining the DNA fragment 3 in Example A-1(a) but using the DNA fragments 7 and 8 and the antisense primer 3, obtained above, for the DNA fragments 1 and 2 and the antisense primer 2, respectively. The PCR resulted in obtaining a DNA fragment (the DNA fragment 9) comprising the nucleotide sequence of SEQ ID NO:29.

A PCR was performed similarly as that for obtaining the DNA fragment 4 in Example A-1(a) but using the DNA fragment 9 for the DNA fragment 3, the antisense primer 3 for the antisense primer 2, and an oligonucleotide with the nucleotide sequence of 5'-GGCCCACTTCACGCTA-CAACC-3' (SEQ ID NO:48) for the mutagenic sense primer, to replace 103rd and 104th nucleotides of thymine and guanine in SEQ ID NO:29 with a guanine and cytosine, respectively. The PCR resulted in obtaining a DNA fragment (the DNA fragment 10) comprising a nucleotide sequence identical to 91st–570th nucleotides in SEQ ID NO:29 except for the 103rd and 104th replaced with a guanine and a cytosine, respectively.

A PCR was performed similarly as that for obtaining the DNA fragment 5 in Example A-1(a) but using the DNA fragment 9 for the DNA fragment 3, and an oliqonucleotide with the nucleotide sequence of 5'-GGTTGTAGCGT-GAACTCGGCC-3' (SEQ ID NO:49) for the mutagenic antisense primer, to replace 103rd and 104th nucleotides of thymine and guanine in SEQ ID NO:29 with a guanine and cytosine, respectively. The PCR resulted in, obtaining a DNA fragment (the DNA fragment 11) comprising a nucleotide sequence identical to 1st–111th nucleotides in SEQ ID NO:29 except for the 103rd and 104th, replaced with a guanine and cytosine, respectively.

A PCR was performed similarly as that for obtaining the DNA fragment 3 in Example A-1(a) but using the DNA fragments 10 and 11 and the antisense primer 3, obtained above, for the DNA fragments 1 and 2 and the antisense primer, respectively. The PCR resulted in obtaining a DNA fragment (the DNA fragment 12) comprising the nucleotide sequence of SEQ ID NO:22, the nucleotide sequence of SEQ ID NO:24 and a site recognized by a restriction enzyme XhoI, linked to the 5'-terminus of the SEQ ID NO:22, and a termination codon of 5'-TAG-3' and a site recognized by a restriction enzyme NotI, linked to the 3'-terminus of the SEQ ID NO:22.

Figure 10:
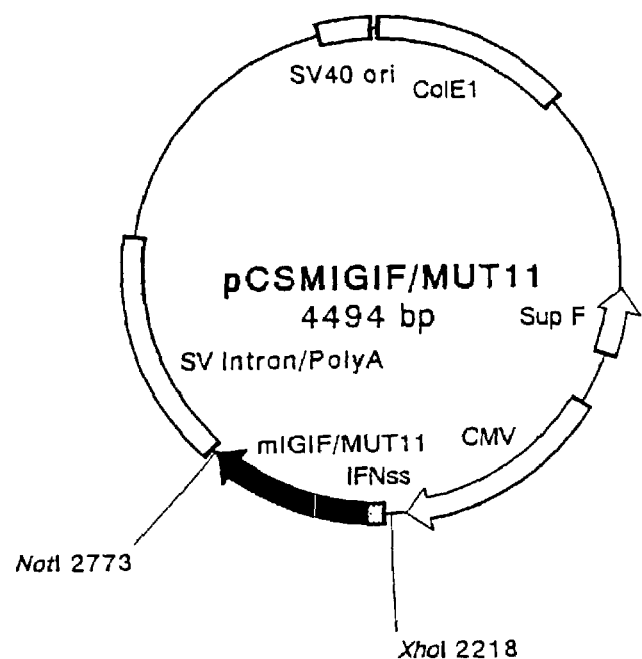
FIG. 10 is the restriction map of a recombinant DNA "pCSMIGIF/MUT11" encoding further another polypeptide according to the present invention.

The DNA fragment 12 was treated similarly as the DNA fragment 6, according the procedure for obtaining the recombinant DNA "pCSHIGIF/MUT12" in Example A-1 (a), to obtain a autonomously replicable recombinant DNA "pCSMIGIF/MUT11". As shown in FIG. 10, in the recombinant DNA "pCSMIGIF/MUT11", a cDNA "mIGIF/MUT11" with the nucleotide sequence of SEQ ID NO:22 was linked to downstream of the nucleotide sequence "IFNss", encoding the signal peptide of the subtype α2b of human interferon-α. As shown in the accompanied amino acid sequence, the SEQ ID NO:22 encodes an amino acid sequence derived from the wild type polypeptide with SEQ ID NO:5 by replacing the cysteine at the 7th position with an alanine.

Figure 11:
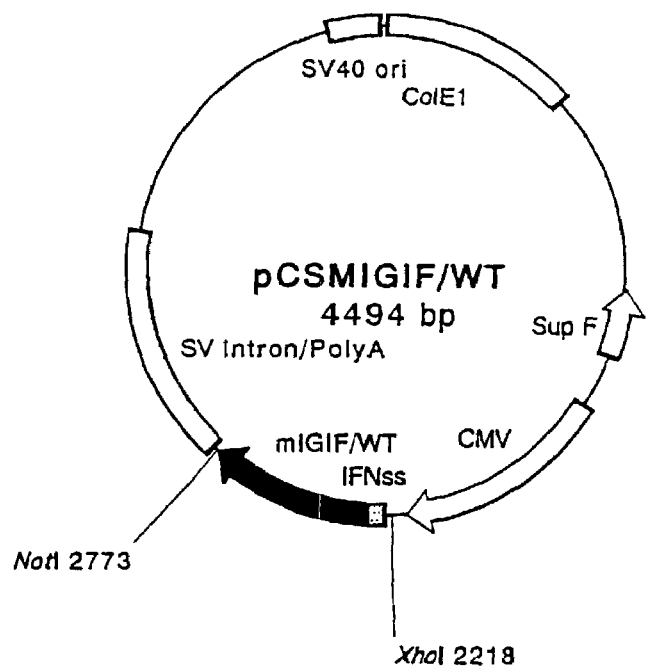
FIG. 11 is the restriction map of a recombinant DNA "pCSMIGIF/WT" encoding the wild-type polypeptide from mouse origin.

For a control, an autonomously replicable recombinant DNA "pCSMIGIF/WT" was prepared similarly as the procedure for obtaining the recombinant DNA "pCSHIGIF/MUT12" but treating the DNA fragment 9 for the DNA fragment 6. As shown in FIG. 11, in the recombinant DNA "pCSMIGIF/WT", a cDNA "mIGIF/WT" with the nucleotide sequence of SEQ ID NO:28, encoding the wild-type polypeptide, was linked to downstream of the nucleotide sequence "IFNss", encoding the signal peptide of subtype α2b of human interferon-α.

EXAMPLE A-8(b)

Production of Polypeptide by Transformant

According to the procedure for the production of the polypeptide in Example A-1(b) but using the recombinant DNA "pCSMIGIF/MUT12" for "pCSHIGIF/MUT11", the recombinant DNA was extracted, the DNA was introduced into COS-1 cells, and the COS-1 cells with the DNA was cultured to obtain a culture. The culture was analyzed by Western blotting using the monoclonal antibody described in Japanese Patent Kokai No. 217,798/96 by the present applicant. The analysis proved that the present polypeptide capable of inducing production of IFN-γ by immunocompetent cells, with the amino acid sequence derived from SEQ ID NO:5 by replacing the cysteine at 7th position with an alanine, was produced in the culture in an amount of about 20 ng/ml.

As a control, treating the recombinant DNA "pCSH-MIGIF/WT" similarly as above produced the wild-type polypeptide capable of inducing production of IFN-γ by immunocompetent cells. The production of the wild-type polypeptide was significantly lower than that obtained by using "pCSMIGIF/MUT11", descrived above. This evidences that the present polypeptide in this Example is more stable and exhibits the biological activities higher than the wild-type polypeptide.

EXAMPLE A-8(c)

Purification of Polypeptide

The culture containing the present polypeptide, in Example A-8(b), was centrifuged to collect a supernatant. The supernatant was fed to a column packed with a gel for immunoaffinity chromatography using the monoclonal antibody, prepared by the method described in Japanese Patent Kokai No. 217,798/96 by the present applicant, and preliminarily washed with PBS. After a fresh PBS was run through the column to wash, 35 mM ethylamine (pH 10.8) was run to elute. From the eluted fractions, those containing the polypeptide capable of inducing production IFN-γ by immunocompetent cells were collected. The collected fractions were dialyzed against PBS at 4° C. for 18 hours, and then concentrated by membrane-filtration followed by lyophilization to obtain a solid polypeptide with a purity of about 95%. In parallel, the culture containing the wild-type polypeptide, obtained by using the recombinant DNA "pCSMIGIF/WT", was purified similarly as above for a control in analyzing the physicochemical properties as described below.

EXAMPLE A-8(d)

Molecular Weight

SDS-Polyacrylamide gel electrophoresis of the present polypeptide in Example A-8(c), similarly as in Example A-1(d), exhibited a main band of polypeptide capable of inducing production at a position corresponding to a molecular weight of about 18,500–19,500 daltons.

EXAMPLE A-8(e)

N-Terminal Amino Acid Sequence

By analyzing similarly as in Example A-1(e), the present polypeptide in Example A-8(c) was proved to contain the amino acid sequence of SEQ ID NO:30 in the N-terminus.

EXAMPLE A-8(f)

Stability

The present polypeptide or the wild-type polypeptide, in Example A-8(c), was dissolved in PBS containing 0.2 g/ml maltose, and the solution was incubated at 40° C. for 24 hours. After 0, 3, 9, or 24 hours from starting the incubation, a portion of each solution was sampled. The samples were individually assayed on IFN-γ inducing activity, according to the methods described below, in Example A-8(g), to study the time course of the activity upon the incubation. Percentage (%) of the residual activity at every point was calculated based on the activity at the starting point. The results are in FIG. 12.

Figure 12:
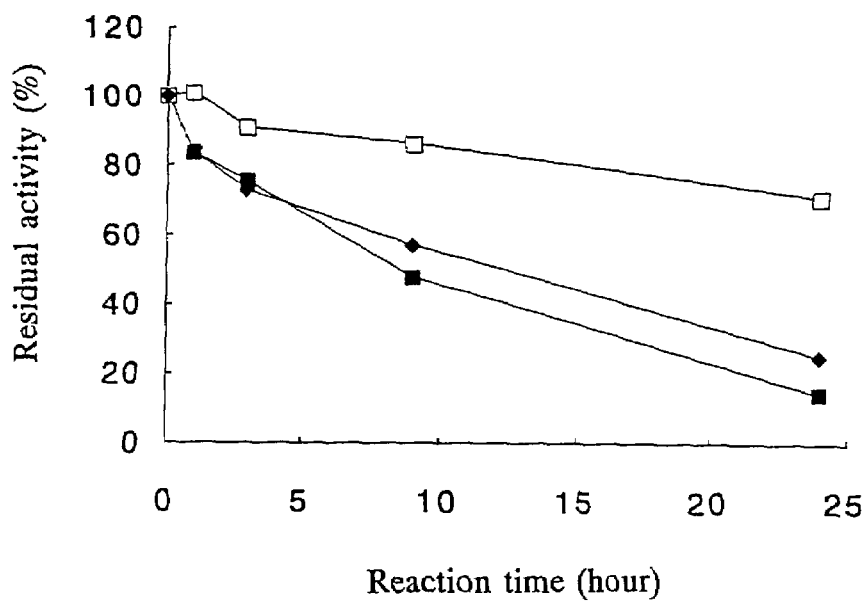
FIG. 12 shows the time course of activity upon incubation of the polypeptides according to the present invention and the wild-type polypeptide, from mouse origin.

As shown in FIG. 12, the present polypeptide in this Example was more stable and retained the activity longer than the wild-type polypeptide. This evidences that the amino acid replacement used in this Example can effectively improve the stability of the wild type polypeptide without reducing the biological activities.

EXAMPLE A-8(g)

Production of IFN-γ by Immunocompetent Cells

Splenocytes were collected from C3H/HeJ mice as immunocompetent cells. The splenocytes were suspended in RPMI-1640 medium supplemented with 10 v/v % fetal bovine serum. The suspensions were given the present polypeptide or the wild-type polypeptide, in Example A-8 (a), in the presence or absence of concanavalin A or interleukin 2. Thereafter, the splenocytes were cultured before examined on productions of IFN-γ by conventional enzyme-immunoassay to evaluate an inducing activity of production of IFN-γ. The present polypeptide proved to act on the splenocytes, immunocompetent cells, to induce the production of IFN-γ. The inducing activity of IFN-γ production of the present polypeptide was equal to or higher than that of the wild-type polypeptide.

EXAMPLE A-8(h)

Acute Toxicity Test

The present polypeptide in Example A-8(a) was examined on the acute toxicity by the method in Example A-1(j). As a result, the $LD_{50}$ of the present polypeptide proved to be about one mg or higher per one kg of the body weight, independently of the administration routs. This evidences that the present polypeptide can be incorporated into pharmaceuticals for mammalian including humans without anxiety.

EXAMPLE A-9

Production of Polypeptide

Figure 13:
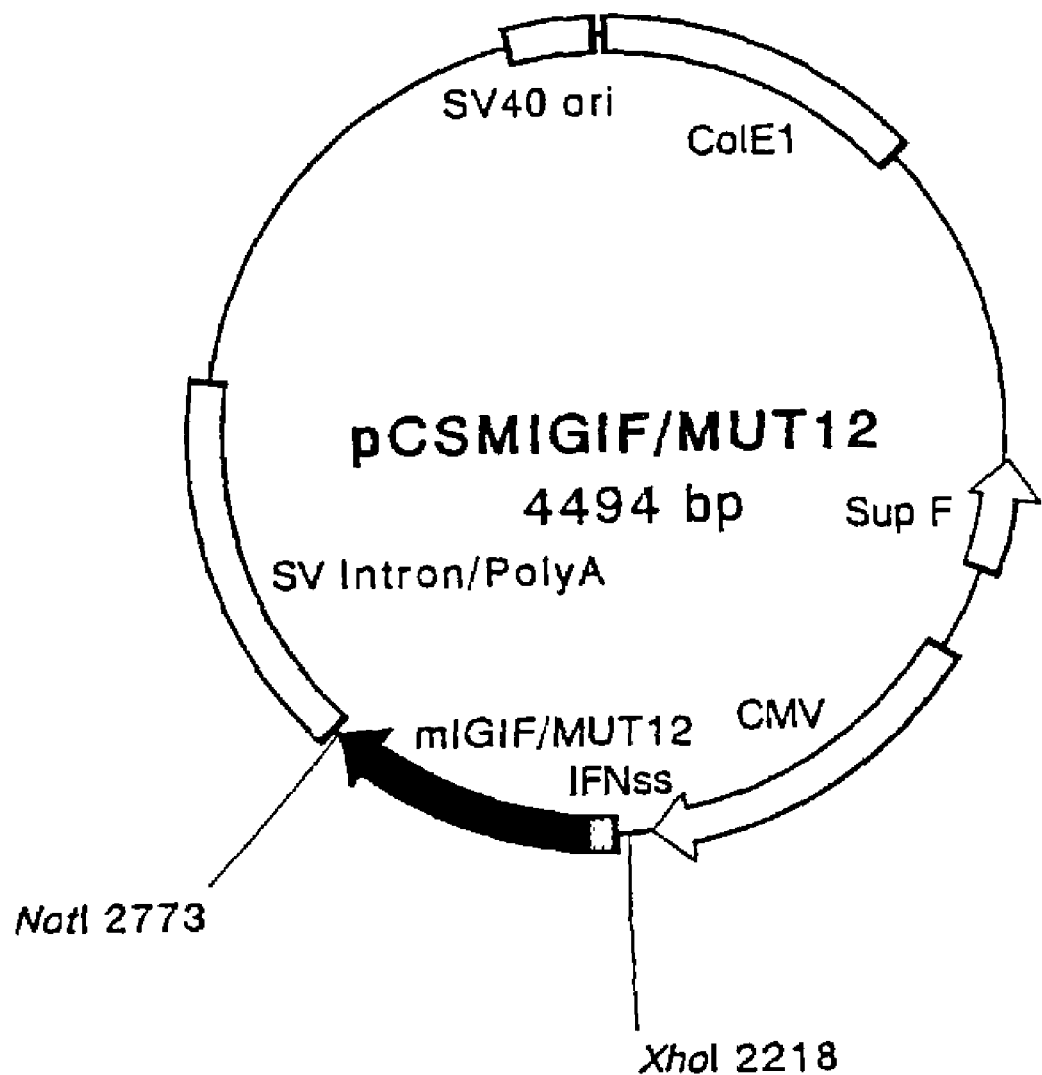
FIG. 13 is the restriction map of a recombinant DNA "pCSMIGIF/MUT12" encoding further another polypeptide according to the present invention.

An autonomously replicable recombinant DNA "pCSMIGIF/MUTl12" containing the nucleotide sequence of SEQ ID NO:23 was obtained by a procedure similar as in Example A-8(a) but using the DNA fragment 9, obtained in Example A-8(a), as a template, and an oligonucleotide with the nucleotide sequence of 5'-GGACACTTTCTTGCTAGC-CAAAAGG-3' (SEQ ID NO:50) and an oligonucleotide with the nucleotide sequence of 5'-CCTTTTGGCTAGCAA-GAAAGTGTCC-3' (SEQ ID NO:51), as a mutagenic sense and a mutagenic antisense primer, respectively, to replace the cysteine at 125th position in SEQ ID NO:5 with a serine. As shown in FIG. 13, in the recombinant DNA "pCSMIGIF/MUTl12", a cDNA "mIGIF/MUT12" encoding the amino acid sequence of SEQ ID NO:14 was linked to downstream of the nucleotide sequence "IFNss", encoding the signal peptide of the subtype a2b of human interferon-α.

The recombinant DNA was introduced into COS-1 cells similarly as in Example A-1(b) to obtain a transformant. Culturing the transformant produced the polypeptide with the amino acid sequence of SEQ ID NO:14 in an amount of about 50 ng per one ml of the culture. The culture was purified before analyzed on the physicochemical properties similarly as in Example A-8. As a result, the polypeptide in this Example proved to be similar to that in Example A-8 in the properties, i.e., the molecular weight, the N-terminal amino acid sequence, and the less toxicity. As shown in FIG. 12, the results of the analysis on stability, obtained according to the method in Example A-8(f), the present polypeptide in this Example was more stable than the wild-type polypeptide. These results evidence that the amino acid replacement used in this Example can effectively improve the stability of the wild type polypeptide without reducing the biological activities.

EXAMPLE B-1

Solution

Any one of the present polypeptides purified in Examples A-1 to A-9 was dissolved in physiological saline containing one v/v % human serum albumin as a stabilizer to give a concentration of one mg/ml, and the solution was membrane-filtered in usual manner into a germ-free solution.

The solutions, with a satisfactory stability, can be used as an injection, an ophthalmic solution, and a collunarium for treating and/or preventing susceptive diseases such as malignant tumors, viral diseases, infections and immunopathies, of mammalian including human.

EXAMPLE B-2

Dry Injection

One hundred mg of any one of the present polypeptides purified in Examples A-1 to A-9 was dissolved in 100 ml of physiological saline containing one w/v % gelatin as a stabilizer, and the solution was sterilized membrane-filtered in usual manner into a germ-free solution. One ml aliquotes of each of the sterilized solutions were distributed to vials, and lyophilized before sealing the vials with caps.

The products, with a satisfactory stability, can be used as a dry injection for treating and/or preventing susceptive diseases such as malignant tumors, viral diseases, infections, and immunopathies of mammalian including human.

EXAMPLE B-3

Ointment

"HI-BIS-WAKO 104", a carboxyvinylpolymer commercialized by Wako Pure Chemicals, Tokyo, Japan, and "TRE- HALOSE", a powdered crystalline trehalose commercialized by Hayashibara Co., Ltd., Okayama, Japan, were dissolved in sterilized distilled water to give concentrations of 1.4 w/w % and 2.0 w/w %, respectively. Any one of the present polypeptides purified in Examples A-1 to A-9 was mixed with the solution into homogeneity. Each of the homogenate was adjusted to pH 7.2 to obtain a paste containing about one mg/g of any one of the polypeptides.

The pastes, with a satisfactory spreadablity and stability, can be used as an ointment for treating and/or preventing susceptive diseases such as malignant tumors, viral diseases, infections and immunopathies, of mammalian including human.

EXAMPLE B-4

Tablet

Any one of the purified polypeptides in Examples A-1 to A-9 and "LUMIN", [bis-4-(1-ethylquinoline)][γ-4'-(1-ethylquinoline)] pentamethionine cyanine, as a cell activator, were mixed with "FINETOSE®", an anhydrous crystalline α-maltose commercialized by Hayashibara Co., Ltd., Okayama, Japan, into homogeneity. Each of the homogenate was processed with a conventional tablet machine into tablets, each of which weighed 200 mg and contained about one mg of any of the polypeptides and the LUMIN.

The tablets with a satisfactory swallowability, stability and cell-activating activity can be used as a tablet for treating and/or preventing susceptive diseases such as malignant tumors, viral diseases, infections and immunopathies, of mammalian including human.

EXAMPLE B-5

Adoptive Immunotherapeutic Agent

Mononuclear cells were isolated from a peripheral blood of a patient with malignant lymphoma. The cells were suspended in RPMI-1640 medium supplemented with 10 v/v % human AB serum, preheated at 37° C., to give a density of $1 \times 10^6$ cells/ml. To the cell suspension, any one of the present polypeptides in Examples A-1 to A-7 and a recombinant human interleukin 2 were added as adoptive immunotherapeutic agent to give concentrations of 10 ng/ml and 100 units/ml, respectively, before the cells were cultured at 37° C. for one week in a 5 v/v % $CO_2$ incubator. Thereafter, the culture was centrifuged to collect LAK cells.

The LAK cells can exhibit so strong cytotoxicity to the lymphoma when returned to the patient, and an adoptive immunotherapy using the present agent can exert significantly higher effect than that using the interleukin 2 alone. Cytotoxic T cells obtained similarly as above excepting the mononuclear cells, replaced with tumor-invasive lymphocytes, also can effect as equivalent to that of the LAK cells, when returned to the patient. Thus the adoptive immunotherapeutic agent in this Example can be effectively applied to solid malignant tumors such as renal cancer, malignant melanoma, colonic cancer, rectal cancer, and lung cancer, besides malignant lymphomas.

IFN-γ is well known to be involved in protection against infections of virus and bacteria, etc., inhibition of malignant tumors proliferation, regulation of immune system causing protection, and inhibition of immunoglobulin E antibodies production. And IFN-γ is now in use for agents against human susceptive diseases, stating that the directions for the targeting diseases, uses, dosages, and safeness have been already established.

As described in a publication as Frances R. Balkwill, *Saitokain-To-Ganchiryo* (*Cytokines in Cancer Therapy*), Yoshihiko WATANABE tr., (Tokyo, Japan: Tokoyo Kagaku Dojin Co., Ltd., 1991), therapies using killer cells such as NK cells and LAK cells that include antitumor immunotherapies are applied to human diseases, resulting in satisfactory effects as a whole. Recently, an intensive interest is taken in the involvement of the killer cells, which have cytotoxicities enhanced by cytokines, or which are formed induced by cytokines, in therapeutic effects. For example, T. Fujioka et al., *British Journal of Urology*, Vol. 73, No. 1, pp. 23–31 (1994) describes that in an antitumor immunotherapy using both LAK cells and interleukin 2, the interleukin 2 induced formation of the LAK cells, resulting in remarkable effects against human cancer metastases without exhibiting serious toxicities and side effects.

Thus, it has been revealed that IFN-γ or killer cells are involved in treatment and/or prevention of a variety of human diseases, and can contribute to cure or remission to the diseases. As shown in Examples A-1 to A-9, the present polypeptides induce the production of IFN-γ by immunocompetent cells, enhance the cytotoxicity of NK cells, and induce the formation of LAK cells, indicating that the present agents for susceptive diseases can be administered to patients successively for a relatively-long period of time, and effect to treat and/or prevent diseases, in which IFN-γ and/or killer cells are involved, without causing serious side effects.

[Effect of the Invention]

As described above, the present invention is made based on the establishment of stable polypeptides capable of inducing production of IFN-γ by immunocompetent cells. The polypeptides according to the present invention are the substances clarified on their amino acid sequence, and feature to retain the biological activities for a relatively-long period in actual use, because of the higher stability than that of the wild-type polypeptide. Thus the present polypeptides provide a variety of uses such as an IFN-γ inducer for producing IFN-γ in cell cultures and an agent for treating and/or preventing diseases sensitive to IFN-γ in general, including viral diseases, infections, malignant tumors, and immunopathies. The agents with the present polypeptides additionally possessing properties of enhancing cytotoxicities and/or inducing formation of killer cells, as effective ingredients, can satisfactorily treat serious diseases such as malignant tumors.

Furthermore, the present polypeptides generally can induce a desired level of IFN-γ with only a slight amount since they have so strong activity of inducing production of IFN-γ. Because of little toxicity, the polypeptides wouldn't cause serious side effects even when administered with relatively-high doses. These give the present polypeptides an advantage of that they can induce a desired level of IFN-γ rapidly without strictly controll on the dosages in actual use. The polypeptides with these usefulness can be easily produced in a desired amount by the present process using recombinant DNA techniques.

The present invention is a significant invention which has a remarkable effect and gives a great contribution to this field.

While there, has been described what is at present considered to be the preferred embodiments of the present invention, it will be understood the various modifications may be made therein, and it is intended to cover in the appended claims all such modifications as fall within the true spirits and scope of the invention.

What is claimed is:

1. An isolated nucleic acid encoding a polypeptide, wherein said polypeptide comprises an amino acid sequence where one or more cysteine residues in the amino acid sequence of either SEQ ID NO:4 or 5 are replaced with other amino acid residues but where the replacement of one or more cysteine residues does not eliminate in said polypeptide the activity of inducing the production of interferon-γ by immunocompetent cells.

2. An isolated nucleic acid, which is complementary to the full length nucleic acid of claim 1.

3. The nucleic acid of claim 1, wherein said polypeptide comprises any one of the amino acid sequences of SEQ ID NO:6 to 14.

4. An isolated nucleic acid, which is complementary to the full length nucleic acid of claim 3.

5. An autonomously replicable vector, comprising the nucleic acid of claim 1.

6. A host cell, which comprises the nucleic acid of claim 1.

7. The host cell of claim 6, which is of a mammalian epithelial, interstitial or hematopoietic cell origin.

8. A process for producing a polypeptide encoded by the isolated nucleic acid of claim 1, comprising:
   culturing the host cell comprising the nucleic acid of claim 1 to produce said polypeptide; and
   collecting a produced polypeptide from the resulting culture.

9. The process of claim 8, wherein the host cell is of a mammalian epithelial, interstitial or hematopoietic origin.

10. The process of claim 8, wherein said polypeptide is collected by one or more techniques selected from the group consisting of dialysis, salting out, filtration, concentration, fractional precipitation, ion-exchange chromatography, isoelectric focusing chromatography, hydrophobic chromatography, reversed phase chromatography, affinity chromatography, gel electrophoresis, and isoelectric focusing gel electrophoresis.

11. The process of claim 8, wherein said polypeptide is collected by immunoaffinity chromatography using a monoclonal antibody.

* * * * *

SEQUENCE LISTING (1) GENERAL INFORMATION:

(iii) NUMBER OF SEQUENCES: 51

(2) INFORMATION FOR SEQ ID NO: 1:

(i) SEQUENCE CHARACTERISTICS:
       (A) LENGTH: 6 amino acids
       (B) TYPE: amino acid
       (D) TOPOLOGY: linear (ii) MOLECULE TYPE: peptide (xi) SEQUENCE DESCRIPTION: SEQ ID NO: 1:

Asn Asp Gln Val Leu Phe
1               5

(2) INFORMATION FOR SEQ ID NO: 2:

(i) SEQUENCE CHARACTERISTICS:
       (A) LENGTH: 6 amino acids
       (B) TYPE: amino acid
       (D) TOPOLOGY: linear (ii) MOLECULE TYPE: peptide (xi) SEQUENCE DESCRIPTION: SEQ ID NO: 2:

Phe Glu Asp Met Thr Asp
1               5

(2) INFORMATION FOR SEQ ID NO: 3:

(i) SEQUENCE CHARACTERISTICS:
       (A) LENGTH: 5 amino acids
       (B) TYPE: amino acid
       (D) TOPOLOGY: linear (ii) MOLECULE TYPE: peptide (xi) SEQUENCE DESCRIPTION: SEQ ID NO: 3:

Met Tyr Lys Asp Ser
1               5

(2) INFORMATION FOR SEQ ID NO: 4:

(i) SEQUENCE CHARACTERISTICS:
       (A) LENGTH: 157 amino acids
       (B) TYPE: amino acid
       (D) TOPOLOGY: linear (ii) MOLECULE TYPE: peptide (xi) SEQUENCE DESCRIPTION: SEQ ID NO: 4:

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

```
Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Leu
130                 135                 140

Gly Asp Arg Ser Ile Met Phe Thr Val Gln Asn Glu Asp
145                 150                 155
```

(2) INFORMATION FOR SEQ ID NO: 5:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 5:

```
Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
            35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
            115                 120                 125

Asp Asp Ala Phe Lys Leu Ile Leu Lys Lys Asp Glu Asn Gly Asp
130                 135                 140

Lys Ser Val Met Phe Thr Leu Thr Asn Leu His Gln Ser
145                 150                 155
```

(2) INFORMATION FOR SEQ ID NO: 6:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 6:

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
```

```
                    50                    55                    60
Ser Val Lys Ser Glu Lys Ile Ser Thr Leu Ser Cys Glu Asn Lys Ile
 65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
                115                 120                 125

Lys Glu Arg Asp Leu Phe Lys Leu Ile Leu Lys Lys Glu Asp Glu Leu
                130                 135                 140

Gly Asp Arg Ser Ile Met Phe Thr Val Gln Asn Glu Asp
145                 150                 155

(2) INFORMATION FOR SEQ ID NO: 7:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 7:

Tyr Phe Gly Lys Leu Glu Ser Lys Leu Ser Val Ile Arg Asn Leu Asn
 1                   5                  10                  15

Asp Gln Val Leu Phe Ile Asp Gln Gly Asn Arg Pro Leu Phe Glu Asp
                 20                  25                  30

Met Thr Asp Ser Asp Ser Arg Asp Asn Ala Pro Arg Thr Ile Phe Ile
                 35                  40                  45

Ile Ser Met Tyr Lys Asp Ser Gln Pro Arg Gly Met Ala Val Thr Ile
                 50                  55                  60

Ser Val Lys Ser Glu Lys Ile Ser Thr Leu Ser Cys Glu Asn Lys Ile
 65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
                115                 120                 125

Lys Glu Arg Asp Leu Phe Lys Leu Ile Leu Lys Lys Glu Asp Glu Leu
                130                 135                 140

Gly Asp Arg Ser Ile Met Phe Thr Val Gln Asn Glu Asp
145                 150                 155

(2) INFORMATION FOR SEQ ID NO: 8:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 8:

Tyr Phe Gly Lys Leu Glu Ser Lys Leu Ser Val Ile Arg Asn Leu Asn
 1                   5                  10                  15

Asp Gln Val Leu Phe Ile Asp Gln Gly Asn Arg Pro Leu Phe Glu Asp
                 20                  25                  30
```

```
Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
         50                  55                  60

Ser Val Lys Ser Glu Lys Ile Ser Thr Leu Ser Cys Glu Asn Lys Ile
 65              70                  75                      80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Ser Glu
                115                 120                 125

Lys Glu Arg Asp Leu Phe Lys Leu Ile Leu Lys Lys Glu Asp Glu Leu
                130                 135                 140

Gly Asp Arg Ser Ile Met Phe Thr Val Gln Asn Glu Asp
145                 150                 155
```

(2) INFORMATION FOR SEQ ID NO: 9:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 9:

```
Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
             20                  25                  30

Met Thr Asp Ser Asp Ser Arg Asp Asn Ala Pro Arg Thr Ile Phe Ile
            35                  40                  45

Ile Ser Met Tyr Lys Asp Ser Gln Pro Arg Gly Met Ala Val Thr Ile
         50                  55                  60

Ser Val Lys Ser Glu Lys Ile Ser Thr Leu Ser Cys Glu Asn Lys Ile
 65              70                  75                      80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Ser Glu
                115                 120                 125

Lys Glu Arg Asp Leu Phe Lys Leu Ile Leu Lys Lys Glu Asp Glu Leu
                130                 135                 140

Gly Asp Arg Ser Ile Met Phe Thr Val Gln Asn Glu Asp
145                 150                 155
```

(2) INFORMATION FOR SEQ ID NO: 10:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 10:

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Ser Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Ser Glu Lys Ile Ser Thr Leu Ser Ser Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Ser Glu
            115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155
```

(2) INFORMATION FOR SEQ ID NO: 11:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 11:

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Ser Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Ser Glu Lys Ile Ser Thr Leu Ser Ala Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155
```

(2) INFORMATION FOR SEQ ID NO: 12:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 12:

```
Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Ser Arg Asp Asn Ala Pro Arg Thr Ile Phe Ile
                35                  40                  45

Ile Ser Met Tyr Lys Asp Ser Gln Pro Arg Gly Met Ala Val Thr Ile
50                  55                      60

Ser Val Lys Ser Glu Lys Ile Ser Thr Leu Ser Ala Glu Asn Lys Ile
65              70                      75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Ser Glu
            115                 120                 125

Lys Glu Arg Asp Leu Phe Lys Leu Ile Leu Lys Lys Glu Asp Glu Leu
130                 135                 140

Gly Asp Arg Ser Ile Met Phe Thr Val Gln Asn Glu Asp
145                 150                 155
```

(2) INFORMATION FOR SEQ ID NO: 13:

(i) SEQUENCE CHARACTERISTICS:
        (A) LENGTH: 157 amino acids
        (B) TYPE: amino acid
        (D) TOPOLOGY: linear (ii) MOLECULE TYPE: peptide (xi) SEQUENCE DESCRIPTION: SEQ ID NO: 13:

```
Asn Phe Gly Arg Leu His Ala Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
                35                  40                  45

Tyr Met Tyr Lys Asp Ser Glu Val Arg Gly Leu Ala Val Thr Leu Ser
50                  55                      60

Val Lys Asp Ser Lys Met Ser Thr Leu Ser Cys Lys Asn Lys Ile Ile
65              70                      75                  80

Ser Phe Glu Glu Met Asp Pro Pro Glu Asn Ile Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Cys Gln Lys Glu
            115                 120                 125

Asp Asp Ala Phe Lys Leu Ile Leu Lys Lys Asp Glu Asn Gly Asp
130                 135                 140

Lys Ser Val Met Phe Thr Leu Thr Asn Leu His Gln Ser
145                 150                 155
```

(2) INFORMATION FOR SEQ ID NO: 14:

(i) SEQUENCE CHARACTERISTICS:
    (A) LENGTH: 157 amino acids
    (B) TYPE: amino acid
    (D) TOPOLOGY: linear (ii) MOLECULE TYPE: peptide (xi) SEQUENCE DESCRIPTION: SEQ ID NO: 14:

```
Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
            20                  25                  30

Thr Asp Ile Asp Gln Ser Ala Ser Glu Pro Gln Thr Arg Leu Ile Ile
        35                  40                  45

Tyr Met Tyr Lys Asp Ser Glu Val Arg Gly Leu Ala Val Thr Leu Ser
    50                  55                  60

Val Lys Asp Ser Lys Met Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asn Lys Met Glu
            100                 105                 110

Phe Glu Ser Ser Leu Tyr Glu Gly His Phe Leu Ala Ser Gln Lys Glu
        115                 120                 125

Asp Asp Ala Phe Lys Leu Ile Leu Lys Lys Lys Asp Glu Asn Gly Asp
    130                 135                 140

Lys Ser Val Met Phe Thr Leu Thr Asn Leu His Gln Ser
145                 150                 155
```

(2) INFORMATION FOR SEQ ID NO: 15:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: mat peptide
        (B) LOCATION: 1..471
        (C) IDENTIFICATION METHOD: S (xi) SEQUENCE DESCRIPTION: SEQ ID NO: 15:

```
TAC TTT GGC AAG CTT GAA TCT AAA TTA TCA GTC ATA AGA AAT TTG AAT      48
Tyr Phe Gly Lys Leu Glu Ser Lys Leu Ser Val Ile Arg Asn Leu Asn
1               5                   10                  15

GAC CAA GTT CTC TTC ATT GAC CAA GGA AAT CGG CCT CTA TTT GAA GAT      96
Asp Gln Val Leu Phe Ile Asp Gln Gly Asn Arg Pro Leu Phe Glu Asp
            20                  25                  30

ATG ACT GAT TCT GAC TGT AGA GAT AAT GCA CCC CGG ACC ATA TTT ATT     144
Met Thr Asp Ser Asp Cys Arg Asp Asn Ala Pro Arg Thr Ile Phe Ile
        35                  40                  45

ATA AGT ATG TAT AAA GAT AGC CAG CCT AGA GGT ATG GCT GTA ACT ATC     192
Ile Ser Met Tyr Lys Asp Ser Gln Pro Arg Gly Met Ala Val Thr Ile
    50                  55                  60

TCT GTG AAG TCT GAG AAA ATT TCA ACT CTC TCC TGT GAG AAC AAA ATT     240
Ser Val Lys Ser Glu Lys Ile Ser Thr Leu Ser Cys Glu Asn Lys Ile
65                  70                  75                  80

ATT TCC TTT AAG GAA ATG AAT CCT CCT GAT AAC ATC AAG GAT ACA AAA     288
```

-continued

```
Ile Ser Phe Lys Glu Met Asn Pro Pro Asp Asn Ile Lys Asp Thr Lys
            85                  90                  95

AGT GAC ATC ATA TTC TTT CAG AGA AGT GTC CCA GGA CAT GAT AAT AAG      336
Ser Asp Ile Ile Phe Phe Gln Arg Ser Val Pro Gly His Asp Asn Lys
            100                 105                 110

ATG CAA TTT GAA TCT TCA TCA TAC GAA GGA TAC TTT CTA GCT TGT GAA      384
Met Gln Phe Glu Ser Ser Ser Tyr Glu Gly Tyr Phe Leu Ala Cys Glu
            115                 120                 125

AAA GAG AGA GAC CTT TTT AAA CTC ATT TTG AAA AAA GAG GAT GAA TTG      432
Lys Glu Arg Asp Leu Phe Lys Leu Ile Leu Lys Lys Glu Asp Glu Leu
            130                 135                 140

GGG GAT AGA TCT ATA ATG TTC ACT GTT CAA AAC GAA GAC                  471
Gly Asp Arg Ser Ile Met Phe Thr Val Gln Asn Glu Asp
145                 150                 155
```

(2) INFORMATION FOR SEQ ID NO: 16:

(i) SEQUENCE CHARACTERISTICS:
       (A) LENGTH: 471 base pairs
       (B) TYPE: nucleic acid
       (C) STRANDEDNESS: double
       (D) TOPOLOGY: linear (ii) MOLECULE TYPE: cDNA (ix) FEATURE:
       (A) NAME/KEY: mat peptide
       (B) LOCATION: 1..471
       (C) IDENTIFICATION METHOD: S (xi) SEQUENCE DESCRIPTION: SEQ ID NO: 16:

```
TAC TTT GGC AAG CTT GAA TCT AAA TTA TCA GTC ATA AGA AAT TTG AAT       48
Tyr Phe Gly Lys Leu Glu Ser Lys Leu Ser Val Ile Arg Asn Leu Asn
1               5                   10                  15

GAC CAA GTT CTC TTC ATT GAC CAA GGA AAT CGG CCT CTA TTT GAA GAT       96
Asp Gln Val leu Phe Ile Asp Gln Gly Asn Arg Pro Leu Phe Glu Asp
            20                  25                  30

ATG ACT GAT TCT GAC TCT AGA GAT AAT GCA CCC CGG ACC ATA TTT ATT      144
Met Thr Asp Ser Asp Ser Arg Asp Asn Ala Pro Arg Thr Ile Phe Ile
            35                  40                  45

ATA AGT ATG TAT AAA GAT AGC CAG CCT AGA GGT ATG GCT GTA ACT ATC      192
Ile Ser Met Tyr Lys Asp Ser Gln Pro Arg Gly Met Ala Val Thr Ile
50                  55                  60

TCT GTG AAG TCT GAG AAA ATT TCA ACT CTC TCC TGT GAG AAC AAA ATT      240
Ser Val Lys Ser Glu Lys Ile Ser Thr Leu Ser Cys Glu Asn Lys Ile
65                  70                  75                  80

ATT TCC TTT AAG GAA ATG AAT CCT CCT GAT AAC ATC AAG GAT ACA AAA      288
Ile Ser Phe Lys Glu Met Asn Pro Pro Asp Asn Ile Lys Asp Thr Lys
            85                  90                  95

AGT GAC ATC ATA TTC TTT CAG AGA AGT GTC CCA GGA CAT GAT AAT AAG      336
Ser Asp Ile Ile Phe Phe Gln Arg Ser Val Pro Gly His Asp Asn Lys
            100                 105                 110

ATG CAA TTT GAA TCT TCA TCA TAC GAA GGA TAC TTT CTA GCT TGT GAA      384
Met Gln Phe Glu Ser Ser Ser Tyr Glu Gly Tyr Phe Leu Ala Cys Glu
            115                 120                 125

AAA GAG AGA GAC CTT TTT AAA CTC ATT TTG AAA AAA GAG GAT GAA TTG      432
Lys Glu Arg Asp Leu Phe Lys Leu Ile Leu Lys Lys Glu Asp Glu Leu
            130                 135                 140

GGG GAT AGA TCT ATA ATG TTC ACT GTT CAA AAC GAA GAC                  471
Gly Asp Arg Ser Ile Met Phe Thr Val Gln Asn Glu Asp
145                 150                 155
```

(2) INFORMATION FOR SEQ ID NO: 17:

```
      (i) SEQUENCE CHARACTERISTICS:
           (A) LENGTH: 471 base pairs
           (B) TYPE: nucleic acid
           (C) STRANDEDNESS: double
           (D) TOPOLOGY: linear (ii) MOLECULE TYPE: cDNA (ix) FEATURE:
           (A) NAME/KEY: mat peptide
           (B) LOCATION: 1..471
           (C) IDENTIFICATION METHOD: S (xi) SEQUENCE DESCRIPTION: SEQ ID NO: 17:

TAC TTT GGC AAG CTT GAA TCT AAA TTA TCA GTC ATA AGA AAT TTG AAT        48
Tyr Phe Gly Lys Leu Glu Ser Lys Leu Ser Val Ile Arg Asn Leu Asn
1               5                   10                  15

GAC CAA GTT CTC TTC ATT GAC CAA GGA AAT CGG CCT CTA TTT GAA GAT        96
Asp Gln Val Leu Phe Ile Asp Gln Gly Asn Arg Pro Leu Phe Glu Asp
                20                  25                  30

ATG ACT GAT TCT GAC TGT AGA GAT AAT GCA CCC CGG ACC ATA TTT ATT       144
Met Thr Asp Ser Asp Cys Arg Asp Asn Ala Pro Arg Thr Ile Phe Ile
            35                  40                  45

ATA AGT ATG TAT AAA GAT AGC CAG CCT AGA GGT ATG GCT GTA ACT ATC       192
Ile Ser Met Tyr Lys Asp Ser Gln Pro Arg Gly Met Ala Val Thr Ile
        50                  55                  60

TCT GTG AAG TCT GAG AAA ATT TCA ACT CTC TCC TGT GAG AAC AAA ATT       240
Ser Val Lys Ser Glu Lys Ile Ser Thr Leu Ser Cys Glu Asn Lys Ile
65              70                  75                  80

ATT TCC TTT AAG GAA ATG AAT CCT CCT GAT AAC ATC AAG GAT ACA AAA       288
Ile Ser Phe Lys Glu Met Asn Pro Pro Asp Asn Ile Lys Asp Thr Lys
                85                  90                  95

AGT GAC ATC ATA TTC TTT CAG AGA AGT GTC CCA GGA CAT GAT AAT AAG       336
Ser Asp Ile Ile Phe Phe Gln Arg Ser Val Pro Gly His Asp Asn Lys
            100                 105                 110

ATG CAA TTT GAA TCT TCA TCA TAC GAA GGA TAC TTT CTA GCT TCT GAA       384
Met Gln Phe Glu Ser Ser Ser Tyr Glu Gly Tyr Phe Leu Ala Ser Glu
        115                 120                 125

AAA GAG AGA GAC CTT TTT AAA CTC ATT TTG AAA AAA GAG GAT GAA TTG       432
Lys Glu Arg Asp Leu Phe Lys Leu Ile Leu Lys Lys Glu Asp Glu Leu
130                 135                 140

GGG GAT AGA TCT ATA ATG TTC ACT GTT CAA AAC GAA GAC                   471
Gly Asp Arg Ser Ile Met Phe Thr Val Gln Asn Glu Asp
145                 150                 155

(2) INFORMATION FOR SEQ ID NO: 18:

(i) SEQUENCE CHARACTERISTICS:
           (A) LENGTH: 471 base pairs
           (B) TYPE: nucleic acid
           (C) STRANDEDNESS: double
           (D) TOPOLOGY: linear (ii) MOLECULE TYPE: cDNA (ix) FEATURE:
           (A) NAME/KEY: mat peptide
           (B) LOCATION: 1..471
           (C) IDENTIFICATION METHOD: S (xi) SEQUENCE DESCRIPTION: SEQ ID NO: 18:

TAC TTT GGC AAG CTT GAA TCT AAA TTA TCA GTC ATA AGA AAT TTG AAT        48
Tyr Phe Gly Lys Leu Glu Ser Lys Leu Ser Val Ile Arg Asn Leu Asn
1               5                   10                  15

GAC CAA GTT CTC TTC ATT GAC CAA GGA AAT CGG CCT CTA TTT GAA GAT        96
```

```
Asp Gln Val Leu Phe Ile Asp Gln Gly Asn Arg Pro Leu Phe Glu Asp
         20                  25                  30

ATG ACT GAT TCT GAC TCT AGA GAT AAT GCA CCC CGG ACC ATA TTT ATT    144
Met Thr Asp Ser Asp Ser Arg Asp Asn Ala Pro Arg Thr Ile Phe Ile
        35                  40                  45

ATA AGT ATG TAT AAA GAT AGC CAG CCT AGA GGT ATG GCT GTA ACT ATC    192
Ile Ser Met Tyr Lys Asp Ser Gln Pro Arg Gly Met Ala Val Thr Ile
     50                  55                  60

TCT GTG AAG TCT GAG AAA ATT TCA ACT CTC TCC TGT GAG AAC AAA ATT    240
Ser Val Lys Ser Glu Lys Ile Ser Thr Leu Ser Cys Glu Asn Lys Ile
 65                  70                  75                  80

ATT TCC TTT AAG GAA ATG AAT CCT CCT GAT AAC ATC AAG GAT ACA AAA    288
Ile Ser Phe Lys Glu Met Asn Pro Pro Asp Asn Ile Lys Asp Thr Lys
                 85                  90                  95

AGT GAC ATC ATA TTC TTT CAG AGA AGT GTC CCA GGA CAT GAT AAT AAG    336
Ser Asp Ile Ile Phe Phe Gln Arg Ser Val Pro Gly His Asp Asn Lys
            100                 105                 110

ATG CAA TTT GAA TCT TCA TCA TAC GAA GGA TAC TTT CTA GCT TCT GAA    384
Met Gln Phe Glu Ser Ser Ser Tyr Glu Gly Tyr Phe Leu Ala Ser Glu
        115                 120                 125

AAA GAG AGA GAC CTT TTT AAA CTC ATT TTG AAA AAA GAG GAT GAA TTG    432
Lys Glu Arg Asp Leu Phe Lys Leu Ile Leu Lys Lys Glu Asp Glu Leu
    130                 135                 140

GGG GAT AGA TCT ATA ATG TTC ACT GTT CAA AAC GAA GAC                471
Gly Asp Arg Ser Ile Met Phe Thr Val Gln Asn Glu Asp
145                 150                 155

(2) INFORMATION FOR SEQ ID NO: 19:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: mat peptide
        (B) LOCATION: 1..471
        (C) IDENTIFICATION METHOD: S (xi) SEQUENCE DESCRIPTION: SEQ ID NO: 19:

TAC TTT GGC AAG CTT GAA TCT AAA TTA TCA GTC ATA AGA AAT TTG AAT     48
Tyr Phe Gly Lys Leu Glu Ser Lys Leu Ser Val Ile Arg Asn Leu Asn
1                5                  10                  15

GAC CAA GTT CTC TTC ATT GAC CAA GGA AAT CGG CCT CTA TTT GAA GAT     96
Asp Gln Val Leu Phe Ile Asp Gln Gly Asn Arg Pro Leu Phe Glu Asp
         20                  25                  30

ATG ACT GAT TCT GAC TCT AGA GAT AAT GCA CCC CGG ACC ATA TTT ATT    144
Met Thr Asp Ser Asp Ser Arg Asp Asn Ala Pro Arg Thr Ile Phe Ile
        35                  40                  45

ATA AGT ATG TAT AAA GAT AGC CAG CCT AGA GGT ATG GCT GTA ACT ATC    192
Ile Ser Met Tyr Lys Asp Ser Gln Pro Arg Gly Met Ala Val Thr Ile
     50                  55                  60

TCT GTG AAG TCT GAG AAA ATT TCA ACT CTC TCC TCT GAG AAC AAA ATT    240
Ser Val Lys Ser Glu Lys Ile Ser Thr Leu Ser Ser Glu Asn Lys Ile
 65                  70                  75                  80

ATT TCC TTT AAG GAA ATG AAT CCT CCT GAT AAC ATC AAG GAT ACA AAA    288
Ile Ser Phe Lys Glu Met Asn Pro Pro Asp Asn Ile Lys Asp Thr Lys
                 85                  90                  95

AGT GAC ATC ATA TTC TTT CAG AGA AGT GTC CCA GGA CAT GAT AAT AAG    336
Ser Asp Ile Ile Phe Phe Gln Arg Ser Val Pro Gly His Asp Asn Lys
```

```
              100                 105                 110
ATG CAA TTT GAA TCT TCA TCA TAC GAA GGA TAC TTT CTA GCT TCT GAA     384
Met Gln Phe Glu Ser Ser Ser Tyr Glu Gly Tyr Phe Leu Ala Ser Glu
        115                 120                 125

AAA GAG AGA GAC CTT TTT AAA CTC ATT TTG AAA AAA GAG GAT GAA TTG     432
Lys Glu Arg Asp Leu Phe Lys Leu Ile Leu Lys Lys Glu Asp Glu Leu
130                 135                 140

GGG GAT AGA TCT ATA ATG TTC ACT GTT CAA AAC GAA GAC                 471
Gly Asp Arg Ser Ile Met Phe Thr Val Gln Asn Glu Asp
145                 150                 155
```

(2) INFORMATION FOR SEQ ID NO: 20:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: mat peptide
        (B) LOCATION: 1..471
        (C) IDENTIFICATION METHOD: S (xi) SEQUENCE DESCRIPTION: SEQ ID NO: 20:

```
TAC TTT GGC AAG CTT GAA TCT AAA TTA TCA GTC ATA AGA AAT TTG AAT     48
Tyr Phe Gly Lys Leu Glu Ser Lys Leu Ser Val Ile Arg Asn Leu Asn
1               5                   10                  15

GAC CAA GTT CTC TTC ATT GAC CAA GGA AAT CGG CCT CTA TTT GAA GAT     96
Asp Gln Val Leu Phe Ile Asp Gln Gly Asn Arg Pro Leu Phe Glu Asp
            20                  25                  30

ATG ACT GAT TCT GAC TCT AGA GAT AAT GCA CCC CGG ACC ATA TTT ATT    144
Met Thr Asp Ser Asp Ser Arg Asp Asn Ala Pro Arg Thr Ile Phe Ile
            35                  40                  45

ATA AGT ATG TAT AAA GAT AGC CAG CCT AGA GGT ATG GCT GTA ACT ATC    192
Ile Ser Met Tyr Lys Asp Ser Gln Pro Arg Gly Met Ala Val Thr Ile
50                  55                  60

TCT GTG AAG TCT GAG AAA ATT TCA ACT CTC TCC GCT GAG AAC AAA ATT    240
Ser Val Lys Ser Glu Lys Ile Ser Thr Leu Ser Ala Glu Asn Lys Ile
65                  70                  75                  80

ATT TCC TTT AAG GAA ATG AAT CCT CCT GAT AAC ATC AAG GAT ACA AAA    288
Ile Ser Phe Lys Glu Met Asn Pro Pro Asp Asn Ile Lys Asp Thr Lys
                85                  90                  95

AGT GAC ATC ATA TTC TTT CAG AGA AGT GTC CCA GGA CAT GAT AAT AAG    336
Ser Asp Ile Ile Phe Phe Gln Arg Ser Val Pro Gly His Asp Asn Lys
            100                 105                 110

ATG CAA TTT GAA TCT TCA TCA TAC GAA GGA TAC TTT CTA GCT TGT GAA    384
Met Gln Phe Glu Ser Ser Ser Tyr Glu Gly Tyr Phe Leu Ala Cys Glu
        115                 120                 125

AAA GAG AGA GAC CTT TTT AAA CTC ATT TTG AAA AAA GAG GAT GAA TTG    432
Lys Glu Arg Asp Leu Phe Lys Leu Ile Leu Lys Lys Glu Asp Glu Leu
130                 135                 140

GGG GAT AGA TCT ATA ATG TTC ACT GTT CAA AAC GAA GAC                471
Gly Asp Arg Ser Ile Met Phe Thr Val Gln Asn Glu Asp
145                 150                 155
```

(2) INFORMATION FOR SEQ ID NO: 21:

(i) SEQUENCE CHARACTERISTICS:
        (A) LENGTH: 471 base pairs
        (B) TYPE: nucleic acid
        (C) STRANDEDNESS: double -continued (D) TOPOLOGY: linear (ii) MOLECULE TYPE: cDNA (ix) FEATURE:
   (A) NAME/KEY: mat peptide
   (B) LOCATION: 1..471
   (C) IDENTIFICATION METHOD: S (xi) SEQUENCE DESCRIPTION: SEQ ID NO: 21:

```
TAC TTT GGC AAG CTT GAA TCT AAA TTA TCA GTC ATA AGA AAT TTG AAT    48
Tyr Phe Gly Lys Leu Glu Ser Lys Leu Ser Val Ile Arg Asn Leu Asn
 1               5                  10                  15

GAC CAA GTT CTC TTC ATT GAC CAA GGA AAT CGG CCT CTA TTT GAA GAT    96
Asp Gln Val Leu Phe Ile Asp Gln Gly Asn Arg Pro Leu Phe Glu Asp
            20                  25                  30

ATG ACT GAT TCT GAC TCT AGA GAT AAT GCA CCC CGG ACC ATA TTT ATT   144
Met Thr Asp Ser Asp Ser Arg Asp Asn Ala Pro Arg Thr Ile Phe Ile
        35                  40                  45

ATA AGT ATG TAT AAA GAT AGC CAG CCT AGA GGT ATG GCT GTA ACT ATC   192
Ile Ser Met Tyr Lys Asp Ser Gln Pro Arg Gly Met Ala Val Thr Ile
    50                  55                  60

TCT GTG AAG TCT GAG AAA ATT TCA ACT CTC TCC GCT GAG AAC AAA ATT   240
Ser Val Lys Ser Glu Lys Ile Ser Thr Leu Ser Ala Glu Asn Lys Ile
65                  70                  75                  80

ATT TCC TTT AAG GAA ATG AAT CCT CCT GAT AAC ATC AAG GAT ACA AAA   288
Ile Ser Phe Lys Glu Met Asn Pro Pro Asp Asn Ile Lys Asp Thr Lys
                85                  90                  95

AGT GAC ATC ATA TTC TTT CAG AGA AGT GTC CCA GGA CAT GAT AAT AAG   336
Ser Asp Ile Ile Phe Phe Gln Arg Ser Val Pro Gly His Asp Asn Lys
            100                 105                 110

ATG CAA TTT GAA TCT TCA TCA TAC GAA GGA TAC TTT CTA GCT TCT GAA   384
Met Gln Phe Glu Ser Ser Ser Tyr Glu Gly Tyr Phe Leu Ala Ser Glu
        115                 120                 125

AAA GAG AGA GAC CTT TTT AAA CTC ATT TTG AAA AAA GAG GAT GAA TTG   432
Lys Glu Arg Asp Leu Phe Lys Leu Ile Leu Lys Lys Glu Asp Glu Leu
    130                 135                 140

GGG GAT AGA TCT ATA ATG TTC ACT GTT CAA AAC GAA GAC               471
Gly Asp Arg Ser Ile Met Phe Thr Val Gln Asn Glu Asp
145                 150                 155
```

(2) INFORMATION FOR SEQ ID NO: 22:

(i) SEQUENCE CHARACTERISTICS:
      (A) LENGTH: 471 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: mat peptide
      (B) LOCATION: 1..471
      (C) IDENTIFICATION METHOD: S (xi) SEQUENCE DESCRIPTION: SEQ ID NO: 22:

```
AAC TTT GGC CGA CTT CAC GCT ACA ACC GCA GTA ATA CGG AAT ATA AAT    48
Asn Phe Gly Arg Leu His Ala Thr Thr Ala Val Ile Arg Asn Ile Asn
 1               5                  10                  15

GAC CAA GTT CTC TTC GTT GAC AAA AGA CAG CCT GTG TTC GAG GAT ATG    96
Asp Gln Val Leu Phe Val Asp Lys Arg Gln Pro Val Phe Glu Asp Met
            20                  25                  30

ACT GAT ATT GAT CAA AGT GCC AGT GAA CCC CAG ACC AGA CTG ATA ATA   144
Thr Asp Ile Asp Gln Ser Ala Ser Glu Pro Gln Thr Arg Leu Ile Ile
```

```
              35                  40                  45
TAC ATG TAC AAA GAC AGT GAA GTA AGA GGA CTG GCT GTG ACC CTC TCT      192
Tyr Met Tyr Lys Asp Ser Glu Val Arg Gly Leu Ala Val Thr Leu Ser
         50                  55                  60

GTG AAG GAT AGT AAA ATG TCT ACC CTC TCC TGT AAG AAC AAG ATC ATT      240
Val Lys Asp Ser Lys Met Ser Thr Leu Ser Cys Lys Asn Lys Ile Ile
 65                  70                  75                  80

TCC TTT GAG GAA ATG GAT CCA CCT GAA AAT ATT GAT GAT ATA CAA AGT      288
Ser Phe Glu Glu Met Asp Pro Pro Glu Asn Ile Asp Asp Ile Gln Ser
                 85                  90                  95

GAT CTC ATA TTC TTT CAG AAA CGT GTT CCA GGA CAC AAC AAG ATG GAG      336
Asp Leu Ile Phe Phe Gln Lys Arg Val Pro Gly His Asn Lys Met Glu
             100                 105                 110

TTT GAA TCT TCA CTG TAT GAA GGA CAC TTT CTT GCT TGC CAA AAG GAA      384
Phe Glu Ser Ser Leu Tyr Glu Gly His Phe Leu Ala Cys Gln Lys Glu
         115                 120                 125

GAT GAT GCT TTC AAA CTC ATT CTG AAA AAA AAG GAT GAA AAT GGG GAT      432
Asp Asp Ala Phe Lys Leu Ile Leu Lys Lys Lys Asp Glu Asn Gly Asp
130                 135                 140

AAA TCT GTA ATG TTC ACT CTC ACT AAC TTA CAT CAA AGT                  471
Lys Ser Val Met Phe Thr Leu Thr Asn Leu His Gln Ser
145                 150                 155

(2) INFORMATION FOR SEQ ID NO: 23:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: mat peptide
        (B) LOCATION: 1..471
        (C) IDENTIFICATION METHOD: S (xi) SEQUENCE DESCRIPTION: SEQ ID NO: 23:

AAC TTT GGC CGA CTT CAC TGT ACA ACC GCA GTA ATA CGG AAT ATA AAT       48
Asn Phe Gly Arg Leu His Cys Thr Thr Ala Val Ile Arg Asn Ile Asn
 1                   5                  10                  15

GAC CAA GTT CTC TTC GTT GAC AAA AGA CAG CCT GTG TTC GAG GAT ATG       96
Asp Gln Val Leu Phe Val Asp Lys Arg Gln Pro Val Phe Glu Asp Met
                 20                  25                  30

ACT GAT ATT GAT CAA AGT GCC AGT GAA CCC CAG ACC AGA CTG ATA ATA      144
Thr Asp Ile Asp Gln Ser Ala Ser Glu Pro Gln Thr Arg Leu Ile Ile
             35                  40                  45

TAC ATG TAC AAA GAC AGT GAA GTA AGA GGA CTG GCT GTG ACC CTC TCT      192
Tyr Met Tyr Lys Asp Ser Glu Val Arg Gly Leu Ala Val Thr Leu Ser
         50                  55                  60

GTG AAG GAT AGT AAA ATG TCT ACC CTC TCC TGT AAG AAC AAG ATC ATT      240
Val Lys Asp Ser Lys Met Ser Thr Leu Ser Cys Lys Asn Lys Ile Ile
 65                  70                  75                  80

TCC TTT GAG GAA ATG GAT CCA CCT GAA AAT ATT GAT GAT ATA CAA AGT      288
Ser Phe Glu Glu Met Asp Pro Pro Glu Asn Ile Asp Asp Ile Gln Ser
                 85                  90                  95

GAT CTC ATA TTC TTT CAG AAA CGT GTT CCA GGA CAC AAC AAG ATG GAG      336
Asp Leu Ile Phe Phe Gln Lys Arg Val Pro Gly His Asn Lys Met Glu
             100                 105                 110

TTT GAA TCT TCA CTG TAT GAA GGA CAC TTT CTT GCT AGC CAA AAG GAA      384
Phe Glu Ser Ser Leu Tyr Glu Gly His Phe Leu Ala Ser Gln Lys Glu
         115                 120                 125
```

```
GAT GAT GCT TTC AAA CTC ATT CTG AAA AAA AAG GAT GAA AAT GGG GAT    432
Asp Asp Ala Phe Lys Leu Ile Leu Lys Lys Lys Asp Glu Asn Gly Asp
    130             135             140

AAA TCT GTA ATG TTC ACT CTC ACT AAC TTA CAT CAA AGT                471
Lys Ser Val Met Phe Thr Leu Thr Asn Leu His Gln Ser
145             150             155
```

(2) INFORMATION FOR SEQ ID NO: 24:

(i) SEQUENCE CHARACTERISTICS:
        (A) LENGTH: 69 base pairs
        (B) TYPE: nucleic acid
        (C) STRANDEDNESS: double
        (D) TOPOLOGY: linear (ii) MOLECULE TYPE: Other nucleic acid (ix) FEATURE:
        (A) NAME/KEY: sig peptide
        (B) LOCATION: 1..69
        (C) IDENTIFICATION METHOD: S (xi) SEQUENCE DESCRIPTION: SEQ ID NO: 24:

```
ATGGCCTTGA CCTTTGCTTT ACTGGTGGCC CTCCTGGTGC TCAGCTGCAA GTCAAGCTGC    60

TCTGTGGGC                                                            69
```

(2) INFORMATION FOR SEQ ID NO: 25:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (F) TISSUE TYPE: liver (ix) FEATURE:
        (A) NAME/KEY: mat peptide
        (B) LOCATION: 1..471
        (C) IDENTIFICATION METHOD: E (xi) SEQUENCE DESCRIPTION: SEQ ID NO: 25:

```
TAC TTT GGC AAG CTT GAA TCT AAA TTA TCA GTC ATA AGA AAT TTG AAT     48
Tyr Phe Gly Lys Leu Glu Ser Lys Leu Ser Val Ile Arg Asn Leu Asn
1               5               10              15

GAC CAA GTT CTC TTC ATT GAC CAA GGA AAT CGG CCT CTA TTT GAA GAT     96
Asp Gln Val Leu Phe Ile Asp Gln Gly Asn Arg Pro Leu Phe Glu Asp
                20              25              30

ATG ACT GAT TCT GAC TGT AGA GAT AAT GCA CCC CGG ACC ATA TTT ATT    144
Met Thr Asp Ser Asp Cys Arg Asp Asn Ala Pro Arg Thr Ile Phe Ile
            35              40              45

ATA AGT ATG TAT AAA GAT AGC CAG CCT AGA GGT ATG GCT GTA ACT ATC    192
Ile Ser Met Tyr Lys Asp Ser Gln Pro Arg Gly Met Ala Val Thr Ile
    50              55              60

TCT GTG AAG TGT GAG AAA ATT TCA ACT CTC TCC TGT GAG AAC AAA ATT    240
Ser Val Lys Cys Glu Lys Ile Ser Thr Leu Ser Cys Glu Asn Lys Ile
65              70              75              80

ATT TCC TTT AAG GAA ATG AAT CCT CCT GAT AAC ATC AAG GAT ACA AAA    288
Ile Ser Phe Lys Glu Met Asn Pro Pro Asp Asn Ile Lys Asp Thr Lys
                85              90              95

AGT GAC ATC ATA TTC TTT CAG AGA AGT GTC CCA GGA CAT GAT AAT AAG    336
Ser Asp Ile Ile Phe Phe Gln Arg Ser Val Pro Gly His Asp Asn Lys
```

```
                  100                 105                 110
ATG CAA TTT GAA TCT TCA TCA TAC GAA GGA TAC TTT CTA GCT TGT GAA    384
Met Gln Phe Glu Ser Ser Ser Tyr Glu Gly Tyr Phe Leu Ala Cys Glu
        115                 120                 125

AAA GAG AGA GAC CTT TTT AAA CTC ATT TTG AAA AAA GAG GAT GAA TTG    432
Lys Glu Arg Asp Leu Phe Lys Leu Ile Leu Lys Lys Glu Asp Glu Leu
130                 135                 140

GGG GAT AGA TCT ATA ATG TTC ACT GTT CAA AAC GAA GAC                471
Gly Asp Arg Ser Ile Met Phe Thr Val Gln Asn Glu Asp
145                 150                 155

(2) INFORMATION FOR SEQ ID NO: 26:

(i) SEQUENCE CHARACTERISTICS:
        (A) LENGTH: 570 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: sig peptide
        (B) LOCATION: 1..15
        (C) IDENTIFICATION METHOD: S (xi) SEQUENCE DESCRIPTION: SEQ ID NO: 26:

ACACCTCGAG CCACC ATG GCC TTG ACC TTT GCT TTA CTG GTG GCC CTC CTG    51
              Met Ala Leu Thr Phe Ala Leu Leu Val Ala Leu Leu
                      -20                 -15

GTG CTC AGC TGC AAG TCA AGC TGC TCT GTG GGC TAC TTT GGC AAG CTT     99
Val Leu Ser Cys Lys Ser Ser Cys Ser Val Gly Tyr Phe Gly Lys Leu
        -10                 -5                  1                 5

GAA TCT AAA TTA TCA GTC ATA AGA AAT TTG AAT GAC CAA GTT CTC TTC    147
Glu Ser Lys Leu Ser Val Ile Arg Asn Leu Asn Asp Gln Val Leu Phe
                10                  15                  20

ATT GAC CAA GGA AAT CGG CCT CTA TTT GAA GAT ATG ACT GAT TCT GAC    195
Ile Asp Gln Gly Asn Arg Pro Leu Phe Glu Asp Met Thr Asp Ser Asp
            25                  30                  35

TGT AGA GAT AAT GCA CCC CGG ACC ATA TTT ATT ATA AGT ATG TAT AAA    243
Cys Arg Asp Asn Ala Pro Arg Thr Ile Phe Ile Ile Ser Met Tyr Lys
        40                  45                  50

GAT AGC CAG CCT AGA GGT ATG GCT GTA ACT ATC TCT GTG AAG TGT GAG    291
Asp Ser Gln Pro Arg Gly Met Ala Val Thr Ile Ser Val Lys Cys Glu
    55                  60                  65

AAA ATT TCA ACT CTC TCC TGT GAG AAC AAA ATT ATT TCC TTT AAG GAA    339
Lys Ile Ser Thr Leu Ser Cys Glu Asn Lys Ile Ile Ser Phe Lys Glu
70                  75                  80                  85

ATG AAT CCT CCT GAT AAC ATC AAG GAT ACA AAA AGT GAC ATC ATA TTC    387
Met Asn Pro Pro Asp Asn Ile Lys Asp Thr Lys Ser Asp Ile Ile Phe
                90                  95                  100

TTT CAG AGA AGT GTC CCA GGA CAT GAT AAT AAG ATG CAA TTT GAA TCT    435
Phe Gln Arg Ser Val Pro Gly His Asp Asn Lys Met Gln Phe Glu Ser
            105                 110                 115

TCA TCA TAC GAA GGA TAC TTT CTA GCT TGT GAA AAA GAG AGA GAC CTT    483
Ser Ser Tyr Glu Gly Tyr Phe Leu Ala Cys Glu Lys Glu Arg Asp Leu
        120                 125                 130

TTT AAA CTC ATT TTG AAA AAA GAG GAT GAA TTG GGG GAT AGA TCT ATA    531
Phe Lys Leu Ile Leu Lys Lys Glu Asp Glu Leu Gly Asp Arg Ser Ile
    135                 140                 145

ATG TTC ACT GTT CAA AAC GAA GAC TAGGCGGCCG CGTGT                   570
Met Phe Thr Val Gln Asn Glu Asp
```

-continued

| 150 | 155 |

(2) INFORMATION FOR SEQ ID NO: 27:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: N-terminal fragment (xi) SEQUENCE DESCRIPTION: SEQ ID NO: 27:

```
Tyr Phe Gly Lys Leu Glu Ser Lys Leu Ser
1               5                   10
```

(2) INFORMATION FOR SEQ ID NO: 28:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: mouse
        (F) TISSUE TYPE: liver (ix) FEATURE:
        (A) NAME/KEY: mat peptide
        (B) LOCATION: 1..471
        (C) IDENTIFICATION METHOD: E (xi) SEQUENCE DESCRIPTION: SEQ ID NO: 28:

```
AAC TTT GGC CGA CTT CAC TGT ACA ACC GCA GTA ATA CGG AAT ATA AAT    48
Asn Phe Gly Arg Leu His Cys Thr Thr Ala Val Ile Arg Asn Ile Asn
1               5                   10                  15

GAC CAA GTT CTC TTC GTT GAC AAA AGA CAG CCT GTG TTC GAG GAT ATG    96
Asp Gln Val Leu Phe Val Asp Lys Arg Gln Pro Val Phe Glu Asp Met
            20                  25                  30

ACT GAT ATT GAT CAA AGT GCC AGT GAA CCC CAG ACC AGA CTG ATA ATA    144
Thr Asp Ile Asp Gln Ser Ala Ser Glu Pro Gln Thr Arg Leu Ile Ile
        35                  40                  45

TAC ATG TAC AAA GAC AGT GAA GTA AGA GGA CTG GCT GTG ACC CTC TCT    192
Tyr Met Tyr Lys Asp Ser Glu Val Arg Gly Leu Ala Val Thr Leu Ser
    50                  55                  60

GTG AAG GAT AGT AAA ATG TCT ACC CTC TCC TGT AAG AAC AAG ATC ATT    240
Val Lys Asp Ser Lys Met Ser Thr Leu Ser Cys Lys Asn Lys Ile Ile
65                  70                  75                  80

TCC TTT GAG GAA ATG GAT CCA CCT GAA AAT ATT GAT GAT ATA CAA AGT    288
Ser Phe Glu Glu Met Asp Pro Pro Glu Asn Ile Asp Asp Ile Gln Ser
                85                  90                  95

GAT CTC ATA TTC TTT CAG AAA CGT GTT CCA GGA CAC AAC AAG ATG GAG    336
Asp Leu Ile Phe Phe Gln Lys Arg Val Pro Gly His Asn Lys Met Glu
            100                 105                 110

TTT GAA TCT TCA CTG TAT GAA GGA CAC TTT CTT GCT TGC CAA AAG GAA    384
Phe Glu Ser Ser Leu Tyr Glu Gly His Phe Leu Ala Cys Gln Lys Glu
        115                 120                 125

GAT GAT GCT TTC AAA CTC ATT CTG AAA AAA AAG GAT GAA AAT GGG GAT    432
Asp Asp Ala Phe Lys Leu Ile Leu Lys Lys Lys Asp Glu Asn Gly Asp
    130                 135                 140

AAA TCT GTA ATG TTC ACT CTC ACT AAC TTA CAT CAA AGT                471
Lys Ser Val Met Phe Thr Leu Thr Asn Leu His Gln Ser
```

(2) INFORMATION FOR SEQ ID NO: 29:

(i) SEQUENCE CHARACTERISTICS:
        (A) LENGTH: 570 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: sig peptide
        (B) LOCATION: 1..15
        (C) IDENTIFICATION METHOD: S (xi) SEQUENCE DESCRIPTION: SEQ ID NO: 29:

```
ACACCTCGAG CCACC ATG GCC TTG ACC TTT GCT TTA CTG GTG GCC CTC CTG         51
                Met Ala Leu Thr Phe Ala Leu Leu Val Ala Leu Leu
                    -20                     -15

GTG CTC AGC TGC AAG TCA AGC TGC TCT GTG GGC AAC TTT GGC CGA CTT          99
Val Leu Ser Cys Lys Ser Ser Cys Ser Val Gly Asn Phe Gly Arg Leu
    -10                 -5                  1                   5

CAC TGT ACA ACC GCA GTA ATA CGG AAT ATA AAT GAC CAA GTT CTC TTC         147
His Cys Thr Thr Ala Val Ile Arg Asn Ile Asn Asp Gln Val Leu Phe
                10                  15                  20

GTT GAC AAA AGA CAG CCT GTG TTC GAG GAT ATG ACT GAT ATT GAT CAA         195
Val Asp Lys Arg Gln Pro Val Phe Glu Asp Met Thr Asp Ile Asp Gln
            25                  30                  35

AGT GCC AGT GAA CCC CAG ACC AGA CTG ATA ATA TAC ATG TAC AAA GAC         243
Ser Ala Ser Glu Pro Gln Thr Arg Leu Ile Ile Tyr Met Tyr Lys Asp
        40                  45                  50

AGT GAA GTA AGA GGA CTG GCT GTG ACC CTC TCT GTG AAG GAT AGT AAA         291
Ser Glu Val Arg Gly Leu Ala Val Thr Leu Ser Val Lys Asp Ser Lys
    55                  60                  65

ATG TCT ACC CTC TCC TGT AAG AAC AAG ATC ATT TCC TTT GAG GAA ATG         339
Met Ser Thr Leu Ser Cys Lys Asn Lys Ile Ile Ser Phe Glu Glu Met
70                  75                  80                  85

GAT CCA CCT GAA AAT ATT GAT GAT ATA CAA AGT GAT CTC ATA TTC TTT         387
Asp Pro Pro Glu Asn Ile Asp Asp Ile Gln Ser Asp Leu Ile Phe Phe
                90                  95                  100

CAG AAA CGT GTT CCA GGA CAC AAC AAG ATG GAG TTT GAA TCT TCA CTG         435
Gln Lys Arg Val Pro Gly His Asn Lys Met Glu Phe Glu Ser Ser Leu
            105                 110                 115

TAT GAA GGA CAC TTT CTT GCT TGC CAA AAG GAA GAT GAT GCT TTC AAA         483
Tyr Glu Gly His Phe Leu Ala Cys Gln Lys Glu Asp Asp Ala Phe Lys
        120                 125                 130

CTC ATT CTG AAA AAA AAG GAT GAA AAT GGG GAT AAA TCT GTA ATG TTC         531
Leu Ile Leu Lys Lys Lys Asp Glu Asn Gly Asp Lys Ser Val Met Phe
    135                 140                 145

ACT CTC ACT AAC TTA CAT CAA AGT TAGGCGGCCG CGTGT                        570
Thr Leu Thr Asn Leu His Gln Ser
150                 155
```

(2) INFORMATION FOR SEQ ID NO: 30:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: N-terminal fragment (xi) SEQUENCE DESCRIPTION: SEQ ID NO: 30:

Asn Phe Gly Arg Leu His
 1               5

(2) INFORMATION FOR SEQ ID NO: 31:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 31:

ACACCTCGAG CCACCATGGC CTTGACCTTT GCTTTAAC                           38

(2) INFORMATION FOR SEQ ID NO: 32:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

TTGCCAAAGT AGCCCACAGA GCAGCTTG                                      28

(2) INFORMATION FOR SEQ ID NO: 33:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 33:

CTGCTCTGTG GGCTACTTTG GCAAGCTTGA ATC                                33

(2) INFORMATION FOR SEQ ID NO: 34:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 34:

ACACGCGGCC GCCTAGTCTT CGTTTTGAAC AG                                 32

(2) INFORMATION FOR SEQ ID NO: 35:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 35:

```
CTCTGTGAAG TCTGAGAAAA TTTCAACTC                                              29
```

(2) INFORMATION FOR SEQ ID NO: 36:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 36:

```
GAGTTGAAAT TTTCTCAGAC TTCACAGAG                                              29
```

(2) INFORMATION FOR SEQ ID NO: 37:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 37:

```
CTGATTCTGA CTCTAGATAA TGC                                                    23
```

(2) INFORMATION FOR SEQ ID NO: 38:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 38:

```
GCATTATCTC TAGAGTCAGA ATCAG                                                  25
```

(2) INFORMATION FOR SEQ ID NO: 39:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 39:

```
CTTTCTAGCT TCTGAAAAAG AGAGAG                                                 26
```

(2) INFORMATION FOR SEQ ID NO: 40:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 40:

```
CTCTCTCTTT TTCAGAAGCT AGAAAG                                                 26
```

(2) INFORMATION FOR SEQ ID NO: 41:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 41:

CAACTCTCTC CTCTGAGAAC AA                                                  22

(2) INFORMATION FOR SEQ ID NO: 42:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 42:

TTGTTCTCAG AGGAGAGAGT TG                                                  22

(2) INFORMATION FOR SEQ ID NO: 43:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 43:

CTCTCCGCTG AGAACAAAAT TATTTCC                                             27

(2) INFORMATION FOR SEQ ID NO: 44:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 44:

TTTGTTCTCA GCGGAGAGAG TTG                                                 23

(2) INFORMATION FOR SEQ ID NO: 45:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 45:

CGGCCAAAGT TGCCCACAGA GCGCTTG                                             27

(2) INFORMATION FOR SEQ ID NO: 46:

(i) SEQUENCE CHARACTERISTICS:
            (A) LENGTH: 33 base pairs
            (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO: 46:

CTGCTCTGTG GGCAACTTTG GCCGACTTCA CTG                                 33

(2) INFORMATION FOR SEQ ID NO: 47:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 47:

ACACGCGGCC GCCTAACTTT GATGTAAGTT AG                                  32

(2) INFORMATION FOR SEQ ID NO: 48:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 48:

GGCCGACTTC ACGCTACAAC C                                              21

(2) INFORMATION FOR SEQ ID NO: 49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 49:

GGTTGTAGCG TGAAGTCGGC C                                              21

(2) INFORMATION FOR SEQ ID NO: 50:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 50:

GGACACTTTC TTGCTAGCCA AAAGG                                          25

(2) INFORMATION FOR SEQ ID NO: 51:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA
```

-continued (xi) SEQUENCE DESCRIPTION: SEQ ID NO: 51:

CCTTTTGGCT AGCAAGAAAG TGTCC                                     25